United States Patent
Ferrari et al.

(10) Patent No.: US 9,528,114 B2
(45) Date of Patent: Dec. 27, 2016

(54) METHOD FOR AMPLIFYING LOCUS IN BACTERIAL CELL

(75) Inventors: Eugenio Ferrari, Reggiolo (IT); Caroline M. Peres, Palo Alto, CA (US)

(73) Assignee: DANISCO US INC., Palo Alto, CA (US)

( * ) Notice: Subject to any disclaimer, the term of this patent is extended or adjusted under 35 U.S.C. 154(b) by 370 days.

(21) Appl. No.: 12/934,630

(22) PCT Filed: Mar. 27, 2009

(86) PCT No.: PCT/US2009/038511
§ 371 (c)(1),
(2), (4) Date: May 19, 2011

(87) PCT Pub. No.: WO2009/120929
PCT Pub. Date: Oct. 1, 2009

(65) Prior Publication Data
US 2011/0229938 A1  Sep. 22, 2011

Related U.S. Application Data

(60) Provisional application No. 61/040,456, filed on Mar. 28, 2008.

(51) Int. Cl.
*C12N 15/75* (2006.01)

(52) U.S. Cl.
CPC ..................................... *C12N 15/75* (2013.01)

(58) Field of Classification Search
None
See application file for complete search history.

(56) References Cited

U.S. PATENT DOCUMENTS

| | | | |
|---|---|---|---|
| 4,302,544 A | 11/1981 | Young et al. | |
| 4,450,235 A | 5/1984 | Dean et al. | |
| 4,760,025 A * | 7/1988 | Estell et al. | 510/392 |
| 4,914,031 A | 4/1990 | Zukowski et al. | |
| 4,980,288 A | 12/1990 | Bryan et al. | |
| 5,208,158 A | 5/1993 | Bech et al. | |
| 5,264,366 A | 11/1993 | Ferrari et al. | |
| 5,310,675 A | 5/1994 | Estell et al. | |
| 5,336,611 A | 8/1994 | Van Eekelen et al. | |
| 5,399,283 A | 3/1995 | Stabinsky et al. | |
| 5,441,882 A | 8/1995 | Estell et al. | |
| 5,482,849 A | 1/1996 | Branner et al. | |
| 5,631,217 A | 5/1997 | Branner et al. | |
| 5,665,587 A | 9/1997 | Aaslyng et al. | |
| 5,700,676 A | 12/1997 | Bott et al. | |
| 5,733,753 A | 3/1998 | Jorgensen | |
| 5,741,694 A | 4/1998 | Hastrup et al. | |
| 5,858,757 A | 1/1999 | Von Der Osten et al. | |
| 5,880,080 A | 3/1999 | Amory et al. | |
| 6,197,567 B1 | 3/2001 | Aaslyng et al. | |
| 6,218,165 B1 | 4/2001 | Estell et al. | |
| 6,762,040 B2 | 7/2004 | Rasmussen | |
| 6,808,896 B2 | 10/2004 | Jorgensen | |
| 7,700,322 B2 | 4/2010 | Olsen et al. | |

FOREIGN PATENT DOCUMENTS

| | | |
|---|---|---|
| EP | 0134048 | 3/1985 |
| EP | 0355036 | 2/1990 |
| WO | WO8906279 | 7/1989 |
| WO | WO9310249 | 5/1993 |
| WO | WO9807846 | 2/1998 |
| WO | WO9920726 | 4/1999 |
| WO | WO9920769 | 4/1999 |
| WO | WO9920770 | 4/1999 |
| WO | WO9943835 | 9/1999 |
| WO | WO 01/90393 | * 11/2001 |
| WO | WO0190393 | 11/2001 |
| WO | WO0214490 | 2/2002 |
| WO | WO 2005/042750 | * 5/2005 |
| WO | WO2005042750 | 5/2005 |
| WO | WO2005052146 | 6/2005 |
| WO | WO2006054997 | 5/2006 |

OTHER PUBLICATIONS

Janniere et al., Gene, 40, 1, 47-55, 1985.*
Yu et al., Food Res. Internat. 28, 251-256, 2005.*
Bron et al., Appl. Envir. Microbiol., 68, 11:5663-5670, 2002.*
Manning et al., Proc. Nat. Acad. Sci., USA, 71, 2, pp. 417-421, 1974.*
Leenhouts et al., Appl. and Environ. Microbiol., 55(2):394-400, 1989.
Alting-Mees, et al., pBluescript II: gene mapping vectors, Nucleic Acids Res, (1989), 17:9494.
Arigoni, et al., "The SpoIIE phosphatase, the sporulation septum and the establishment of forespore-specific transcription in Bacillus subtilis: a reassessment", Mol Microbiol, (1999), 31:1407-15.
Berger, et al., "Characterisation of methionine adenosyltransferase from *Mycobacterium smegmatis* and *M. tuberculosis*", BMC Microbiol, (2003), 3:1-13.
Bhikhabhai, et al., "Isolation of cellulolytic enzymes from Trichoderma reesei QM 9414", (1984), J Appl Biochem., 6:336-45.
Binnie, et al., "Expression and characterization of soluble human erythropoietin receptor made in Streptomyces lividans 66", Protein Expr Purif, (1997), 11:271-8. *
Bron, et al., Use of the alr gene as a food-grade selection marker in lactic acid bacteria, Appl Environ Microbiol, (2002), 68:5663-70.
Brumbauer, et al., "Fractionation of cellulase and beta-glucosidase in a Trichoderma reesei culture liquid by use of two-phase partitioning", (1999) Bioseparation 7:287-95.
Bryan, "Protein engineering of subtilisin", Biochim Biophys Acta, (2000), 1543, 203-222.

(Continued)

*Primary Examiner* — Nancy Treptow
(74) *Attorney, Agent, or Firm* — Danisco US Inc.

(57) ABSTRACT

Certain aspects of this disclosure relate to a method of amplifying a genomic locus. In certain embodiments, the method may comprise: a) contacting a population of bacterial host cells with an inhibitor of an essential enzyme, where the bacterial host cells comprise a genomic locus of the structure: $A_1$-P-M-$A_2$, where $A_1$ and $A_2$ are direct repeats, P comprises a coding sequence for a polypeptide, and M comprises a coding sequence for the essential enzyme; and b) selecting for cells that are resistant to the inhibitor; wherein cells that are resistant to the inhibitor have multiple copies of the amplification unit.

16 Claims, 4 Drawing Sheets

(56) References Cited

OTHER PUBLICATIONS

Caldwell, et al., "Correlation between Bacillus subtilis scoC phenotype and gene expression determined using microarrays for transcriptome analysis", J Bacteriol, (2001). 183:7329-40.
Chiang, et al., "Molecular characterization of Plasmodium falciparum S-adenosylmethionine synthetase", Biochem J, (1999), 344-571-6.
Database EMBL. "Aspergillus sojae arf mRNA for alpha-L-arabinofuranosidase, complete cds." Accession No. AB033289, 1999.
Database EMBL. "TrEST-A4294 TrEST-A Hypocrea jecorina cDNA clone Tr-A4294 5' similar to hypothetical protein [Neurospora crassa], mRNA sequence." Accession No. BM077051, 2002.
Database EMBL. "tric010xi01 T.reesei mycelial culture, Version 3 april Hypocrea jecorina cDNA clone tric010xi01, mRNA sequence." Accession No. CB897267, 2003h.
Database EMBL. "tric018xa22 T.reesei mycelial culture, Version 3 april Hypocrea jecorina cDNA clone tric018xa22, mRNA sequence." Accession No. CB899258, 2003b.
Database EMBL. "tric028xe15 T.reesei mycelial culture, Version 3 april Hypocrea jecorina cDNA clone tric028xe15, mRNA sequence." Accession No. CB901909, 2003i.
Database EMBL. "tric029xo22 T.reesei mycelial culture, Version 3 april Hypocrea jecorina cDNA clone tric029xo22, mRNA sequence." Accession No. CB902338, 2003e.
Database EMBL. "tric030xn12 T.reesei mycelial culture, Version 3 april Hypocrea jecorina cDNA clone tric030xn12, mRNA sequence" Accession No. CB902576, 2003k.
Database EMBL. "tric034xk04 T.reesei mycelial culture, Version 3 april Hypocrea jecorina cDNA clone tric034xk04, mRNA sequence." Accession No. CB903438, 2003c.
Database EMBL. "tric035xa22 T.reesei mycelial culture, Version 3 april Hypocrea jecorina cDNA clone tric035xa22, mRNA sequence." Accession No. CB903527, 2003a.
Database EMBL. "tric038x121 T.reesei mycelial culture, Version 3 april Hypocrea jecorina cDNA clone tric038x121, mRNA sequence" Accession No. CB904545, 2003f.
Database EMBL. "tric040xk24 T.reesei mycelial culture, Version 3 april Hypocrea jecorina cDNA clone tric040xk24, mRNA sequence." Accession No. CB904950, 2003d.
Database EMBL. "tric080xd15 T.reesei mycelial culture, Version 3 april Hypocrea jecorina cDNA clone tric080xd15, mRNA sequence." Accession No. CB906767, 2003g.
Database EMBL. "tric082xo13 T.reesei mycelial culture, Version 3 april Hypocrea jecorina cDNA clone tric082xo13, mRNA sequence." Accession No. CB907643, 2003j.
Database EMBL. "Trichoderma viride strain AS 3.3711 endoglucanase III (EGIII) mRNA,complete cds." Accession No. AY343987, 2003l.
Database Genbank. "Bacillus subtilis S-adenosylmethionine synthetase (metE) gene, complete cds, and phosphoenolpyruvate carboxykinase (ppc) and asparagine synthetase (asn) genes, partial cds", Accession No. U52812, 1996.
Database Genbank. "Thermomonospora fusca beta-1,4-endoglucanase precursor (E1) gene, complete cds." Accession No. L20094, 1998.
Database Genbank. "Trichoderma reesei cbh1 gene for cellobiohydrolase I, upstream region." Accession No. D86235, 1997.
Database GenPept. "Alpha-N-arabinofuranosidase (EC 3.2.1.55), STX-IV—Streptomyces thermoviolaceus." Accession No. JC7820, 2002.
Database Genseq. "Trichoderma reesei EST SEQ ID No. 7425." Accession No. AAF14902, 2001.
Database UniProt. "Cip1." Accession No. Q7Z9M9, 2003a.
Database UniProt. "Putative secreted hydrolase." Accession No. O69962, 1998.
Database UniProt. "SubName: Full=Endoglucanase III." Accession No. Q7Z7X2, 2003b.
Database UniProt. "SubName: Full=Putative secreted protein." Accession No. Q9RD58, 2008.
Dehottay, et al., "Nucleotide sequence of the gene encoding the Streptomyces albus G beta-lactamase precursor", Eur J Biochem, (1987), 166:345-50.
Ellouz, et al., "Analytical separation of trichoderma reesei cellulases by ion-exchange fast protein liquid chromatography", J of Chorma, 396:307-17.
Estell, et al., "Engineering an enzyme by site-directed mutagenesis to be resistant to chemical oxidation", J Biol Chem, (1985), 260:6518-21.
Fahnestock, et al., "Expression of the staphylococcal protein A gene in Bacillus subtilis by gene fusions utilizing the promoter from a Bacillus amyloliquefaciens alpha-amylase gene", J Bacteriol, (1986), 165:796-804.
Ferrari, et al., "Isolation of an Alanine Racemase Gene from Bacillus subtilis and its Use for Plasmid Maintenance in B. subtilis", Nature Biotechnol, (1985), 3:1003-7.
Fliess, et al., "Characterization of Cellulases by HPLC Separation", Eur J. Appl Microbiol Biotechnol, (1983), 17:314-18.
Fornwald, et al., "Two promoters, one inducible and one constitutive, control transcription of the Streptomyces lividans galactose operon", Proc Natl Acad Sci, (1987), 84:2130-4.
Goyal, et al., "Characteristics of fungal cellulases", Biores Technol, (1991), 36:37-50.
Gupta, et al., "Bacterial alkaline proteases: molecular approaches and industrial applications", Appl Microbiol Biotechnol, (2002), 59:15-32.
Hoch, et al., "Chromosomal location of pleiotropic negative sporulation mutations in Bacillus subtilis", Genetics, (1973), 73:215-28.
Hopwood, et al., "Regulation of gene expression in antibiotic-producing Streptomyces", Regulation of gene expression, Cambridge Univ Press, (1986), 251-76.
Janniere, et al., "Stable gene amplification in the chromosome of Bacillus subtilis", Gene, (1985), 40:47-55.
Jung, et al., "Integration and amplification of the *Bacillus* sp. 79-23 cellulase gene in the *Bacillus subtilis* 168 chromosome", J Gen Appl Microbiol, (1998), 44:107-11.
Kelland, et al., Analogs of diaminopimelic acid as inhibitors of meso-diaminopimelate decarboxylase from Bacillus sphaericus and wheat germ, J Biol Chem, (1986), 261:13216-23.
Manning, et al., Inhibition of Bacterial Growth by β-chloro-D-alanine, PNAS, (1974), 71:417-21.
Maurer, "Detergent Proteases", Curr Opin Biotechnol, (2004), 15:330-4.
Medve, et al., "Ion-exchange chromatographic purification and quantitative analysis of Trichoderma reesei cellulases cellobiohydrolase I, II and endoglucanase II by fast protein liquid chromatography", J Chromat, (1998), 808:153-65.
Motamedi, et al., "Integrative vectors for heterologous gene expression in *Streptomyces* spp.", Gene, (1995), 160:25-31.
Msadek, et al., "Signal transduction pathway controlling synthesis of a class of degradative enzymes in Bacillus subtilis: expression of the regulatory genes and analysis of mutations in degS and degU", J Bacteriol, (1990), 172:824-34.
Nakamura, et al., "Codon usage tabulated from international DNA sequence databases: status for the year 2000", Nucleic Acids Res, (2000), 28:292.
Olmos, et al., "Effects of the sinR and degU32 (Hy) mutations on the regulation of the aprE gene in Bacillus subtilis", Mol Gen Genet, (1997), 253:562-7.
Palva, "Molecular cloning of alpha-amylase gene from Bacillus amyloliquefaciens and its expression in B. subtilis", Gene, (1982), 19:81-7.
Perego, et al., "The oligopeptide transport system of Bacillus subtilis plays a role in the initiation of sporulation", Mol Microbiol, 5:173-85.
Petit, et al., "Induction of DNA amplification in the Bacillus subtilis chromosome", EMBO J, (1992), 11:1317-26.

(56) References Cited

OTHER PUBLICATIONS

Pulido, et al., "A Bacillus subtilis phage phi 29 transcription terminator is efficiently recognized in Streptomyces lividans", Gene, (1987), 56:277-82.

Sambrook, et al. "Oligonucleotide-mediated mutagenesis", Molecular Cloning: A Laboratory Manual, 2nd ed. New York: Cold Spring Harbor Press, pp. 15.51-15.56, 1989c.

Sambrook, et al., "Splicing signals", Molecular Cloning: A Laboratory Manual, 2nd ed. New York: Cold Spring Harbor Press, pp. 16.7-16.8, 1989d.

Schauer, et al., "*Escherichia coli* glutamyl-tRNA reductase. Trapping the thioester intermediate", J Biol Chem, (2002), 277:48657-63.

Schmitt-John, et al., "Promoter constructions for efficient secretion expression in Streptomyces lividans", Appl Microbiol Biotechnol, (1992), 36:493-8.

Siezen, et al., "Subtilases: the superfamily of subtilisin-like serine proteases", Protein Sci, (1997), 6:501-23.

Simonen, et al., "Protein secretion in *Bacillus* species", Microbiol Rev, (1993), 57:109-37.

Singh, et al., "The high-resolution Structure of LeuB (Rv2995c) from *Mycobacterium tuberculosis*", J Mol Biol, (2005), 346:1-11.

Stahl et al., J. Bacteriol. 1984 158:411-418.

Taguchi, et al., "Analysis of transcriptional control regions in the Streptomyces subtilisin-inhibitor-encoding gene", Gene, (1989), 84:279-86.

Tangney, et al., "A new method for integration and stable DNA amplification in poorly transformable bacilli", FEMS Microbiol Lett, (1995), 125:107-14.

Tomaz, et al., "Studies on the chromatographic fractionation of Trichoderma reesei cellulases by hydrophobic interaction", J Chromatogr, (1999), 865:123-8.

Van Tilbeurgh, et al., "Separation of endo- and exo-type cellulases using a new affinity chromatography method", FEBS Lett., (1984), 169:215-18.

Wang, et al., "Expression and secretion of human atrial natriuretic alpha-factor in Bacillus subtilis using the subtilisin signal peptide", Gene, (1988), 69:39-47.

Xia, et al., "Construction of an integrative food-grade expression system for Bacillus subtilis", Food Research Intl, (2005), 38:251-6.

\* cited by examiner

US 9,528,114 B2

METHOD FOR AMPLIFYING LOCUS IN BACTERIAL CELL

This application claims priority under 35 USC §371 to PCT/US2009/038511 (WO 2009/120929), with an international filing date of 27 Mar. 2009, which claims priority to U.S. 61/040,456, filed 28 Mar. 2008.

SEQUENCE LISTING

The sequence listing submitted via EFS on Apr. 26, 2013, in compliance with 37 C.F.R. §1.52(e), is incorporated herein by reference. The sequence listing text file submitted via EFS contains the file "31147WO-seqlist.txt" created on Apr. 28, 2009, which is 37,321 bytes in size.

FIELD OF THE INVENTION

The present invention provides methods for amplifying a genomic locus without the use of antibiotics. In particular, the invention relates to a method for amplifying in vivo a DNA sequence encoding a polypeptide of interest, a cell harboring multiple copies of said amplified DNA sequence, and a vector harboring a DNA construct to be used in the method. Furthermore, the present invention relates to a method of producing a polypeptide of interest e.g. an enzyme, by culturing a cell as described above.

BACKGROUND

Expression and recombinant production of exogenous polypeptides is a widely used technique. It is well known that cells can be transformed with nucleic acids encoding exogenous polypeptides of interest for expression and production of large quantities of the desired polypeptides. In some applications, the methods are used to produce vast amounts of polypeptide over what would be produced naturally by the originating organism. Indeed, expression of exogenous nucleic acid sequences, as well as over-expression of endogenous sequences have been extensively used in modern biotechnology.

Despite advances in molecular biology and protein engineering, there remains a need for new methods and compositions that increase expression levels of polypeptides in host cells.

SUMMARY OF THE INVENTION

Provided herein is a method of amplifying a genomic locus. In certain embodiments, the method may comprise: a) contacting a population of bacterial host cells with an inhibitor of an essential enzyme, where the bacterial host cells comprise a genomic locus of the structure: $A_1$-P-M-$A_2$, where $A_1$ and $A_2$ are direct repeats, P comprises a coding sequence for a polypeptide of interest, and M comprises a coding sequence for the essential enzyme, and b) selecting for cells that are resistant to the inhibitor; where cells that are resistant to the inhibitor have multiple copies of the amplification unit. The bacterial host cell may be a Bacillus sp. cell, although other bacterial cell types, e.g., Streptomyces sp., are envisioned. In some embodiments, the polypeptide of interest is a subtilisin e.g. the subtilisin of SEQ ID NO:8, or mature form thereof set forth in SEQ ID NO:12. In certain cases, the method avoids the use of antibiotic markers and antibiotics, and provides an alternative to antibiotic-based amplification systems. In certain embodiments, the essential enzyme has the amino acid sequence of an enzyme e.g. a wild-type enzyme, that is endogenous to the cell. In particular embodiments, the bacterial host cell used in the method may or may not contain an inactivated endogenous gene encoding the essential enzyme, where the inactivated gene may be at a different genomic locus to the genomic locus of structure: $A_1$-P-M-$A_2$. In certain cases, the essential enzyme may be alanine racemase e.g. SEQ ID NO:11, and the inhibitor may be β-chloro-D-alanine or cycloserine, although other enzyme/inhibitor combinations may be employed. In some embodiments, the amplification unit comprises the sequence set forth in SEQ ID NO:7.

The amplification unit provides for expression of the essential enzyme encoded by region M. In particular embodiments, M may comprise a coding sequence for the essential enzyme and a promoter operably linked to the coding sequence, wherein the promoter is native to the coding sequence for the essential enzyme. In certain embodiments, the coding sequence and the promoter may be endogenous to the host cell. The amplification unit also provides for expression of the protein of interest encoded by region P. In particular embodiments, the coding sequence of P may be operably linked to an endogenous or non-endogenous promoter that is present in the adjacent direct repeat ($A_1$). In other embodiments, the promoter for P may not be present in the adjacent direct repeat. Rather, the promoter may be present in region P.

In some embodiments, the invention provides a bacterial host cell comprising a genomic locus comprising an amplification unit of the structure: $A_1$-P-M-$A_2$, wherein $A_1$ and $A_2$ are direct repeats, P comprises a coding sequence for a polypeptide of interest, and M comprises a coding sequence for an essential enzyme is also provided. In this embodiment, the amplification unit provides for significant expression of the essential enzyme. The bacterial host cell may be a Bacillus sp. cell, although other bacterial cell types, e.g., Streptomyces sp., are envisioned. In some embodiments, the polypeptide of interest is a subtilisin e.g. the subtilisin of SEQ ID NO:8, or mature form thereof set forth in SEQ ID NO:12. In certain cases, the method avoids the use of antibiotic markers and antibiotics, and provides an alternative to antibiotic-based amplification systems. In certain embodiments, the essential enzyme has the amino acid sequence of an enzyme e.g. a wild-type enzyme, that is endogenous to the cell. In particular embodiments, the bacterial host cell may or may not contain an inactivated endogenous gene encoding the essential enzyme, where the inactivated gene may be at a different genomic locus to the genomic locus of structure: $A_1$-P-M-$A_2$. In certain cases, the essential enzyme may be alanine racemase e.g. SEQ ID NO:11, and the inhibitor may be β-chloro-D-alanine or cycloserine, although other enzyme/inhibitor combinations may be employed. In some embodiments, the amplification unit comprises the sequence set forth in SEQ ID NO:7.

In other embodiments, the bacterial host cell of the invention comprises a genomic locus comprising multiple copies of an amplification unit of the structure: $A_1$-P-M-$A_2$, where $A_1$ and $A_2$ are direct repeats, P comprises a first coding sequence for a polypeptide of interest, and M comprises a second coding sequence of an essential enzyme. In some embodiments, the amplification unit comprises a polynucleotide sequence set forth in SEQ ID NO:7. In some embodiments, the first coding sequence is operably linked to a promoter that is present in direct repeat A1. In particular embodiments, the bacterial host cell comprises a genomic locus comprising multiple copies an amplification unit described by the formula: $(A_1\text{-P-M})_n\text{-}A_2$, where n is at least 2, $A_1$ and $A_2$ are direct repeats, P comprises a coding sequence for a polypeptide of interest, and M encodes an essential enzyme, where the coding sequence of M is operably linked to an endogenous or non-endogenous promoter. In one embodiment, the coding sequence of M and the promoter may be endogenous to the host cell. In some embodiments, the bacterial host cell comprises a genomic locus comprising multiple copies e.g. at least 2 copies, of the amplification unit of SEQ ID NO:7. The amplification unit provides for expression of both the polypeptide of interest e.g. a subtilisin, and the essential enzyme. In some embodiments, the expressed polypeptide of interest is subtilisin FNA set forth in SEQ ID NO:8, or mature form thereof set forth in SEQ ID NO:12, and the essential enzyme is alanine racemase set forth is SEQ ID NO:11. In a particular embodiment, the promoter operably linked to the coding sequence of P may be part of the adjacent direct repeat ($A_1$). In another embodiment, the promoter operably linked to the coding sequence of region P is present in region P rather than in the adjacent direct repeat.

In another embodiment, the invention encompasses a bacterial cell culture that comprises growth medium and a population of bacterial host cells comprising at least one, at least 2 or more copies of the amplification unit of the structure $A_1$-P-M-$A_2$, wherein $A_1$ and $A_2$ are direct repeats, P comprises a first coding sequence for a protein of interest, and M comprises a second coding sequence of an essential enzyme. As described above, the amplification unit provides for expression of both the polypeptide of interest e.g. a subtilisin, and the essential enzyme. In some embodiments, the expressed polypeptide of interest is subtilisin FNA set forth in SEQ ID NO:8, or mature form thereof set forth in SEQ ID NO:12, and the essential enzyme is alanine racemase set forth is SEQ ID NO:11. In yet another embodiment, the bacterial cell culture may be employed in a protein production method that comprises: maintaining a culture of subject cells under conditions suitable to produce the polypeptide of interest encoded by the coding sequence. In particular embodiments, this method may further comprise recovering the polypeptide of interest from the culture medium.

DEFINITIONS

Figure 1:
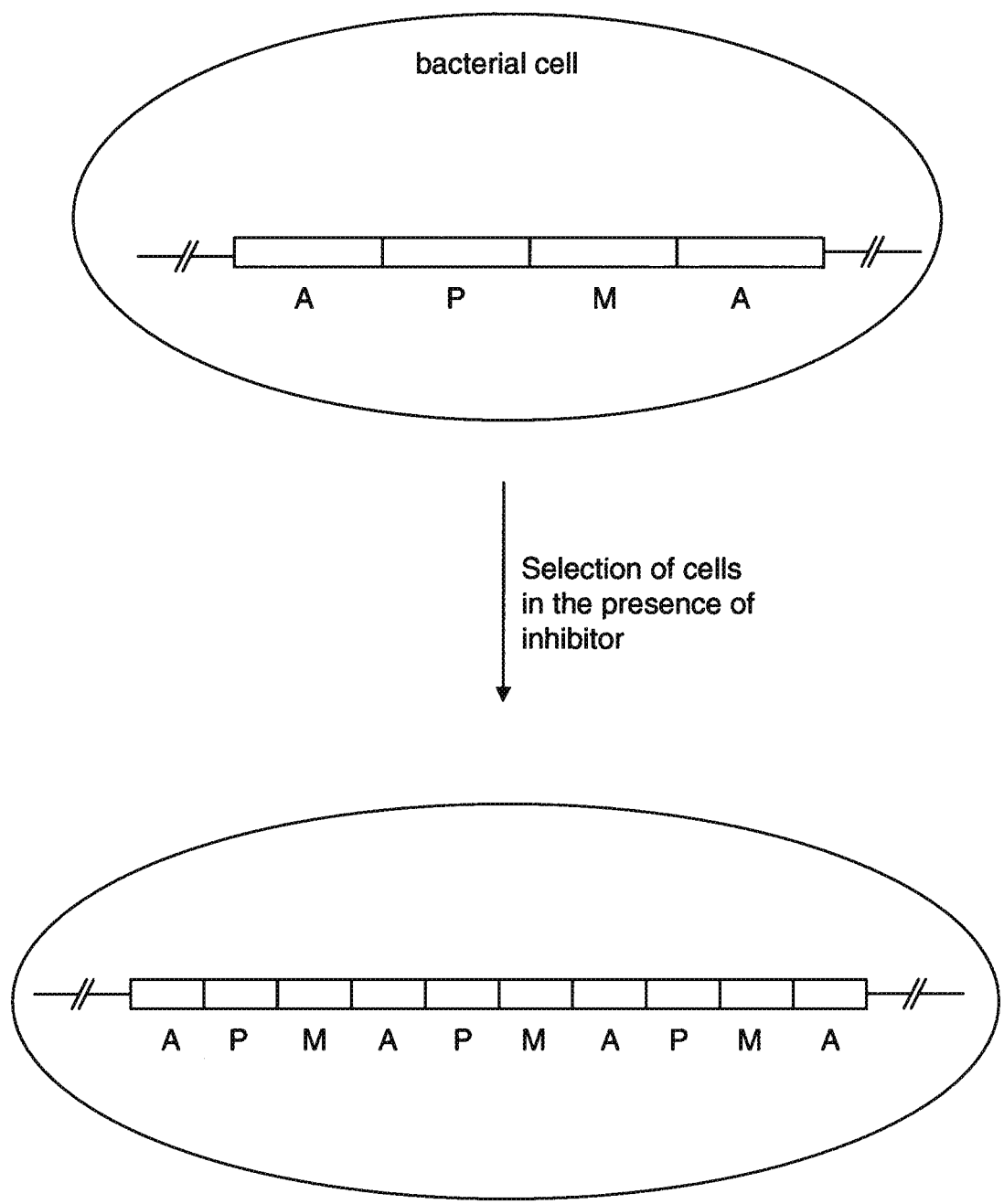
FIG. 1 schematically illustrates some features of embodiments described herein.
Figure 2:
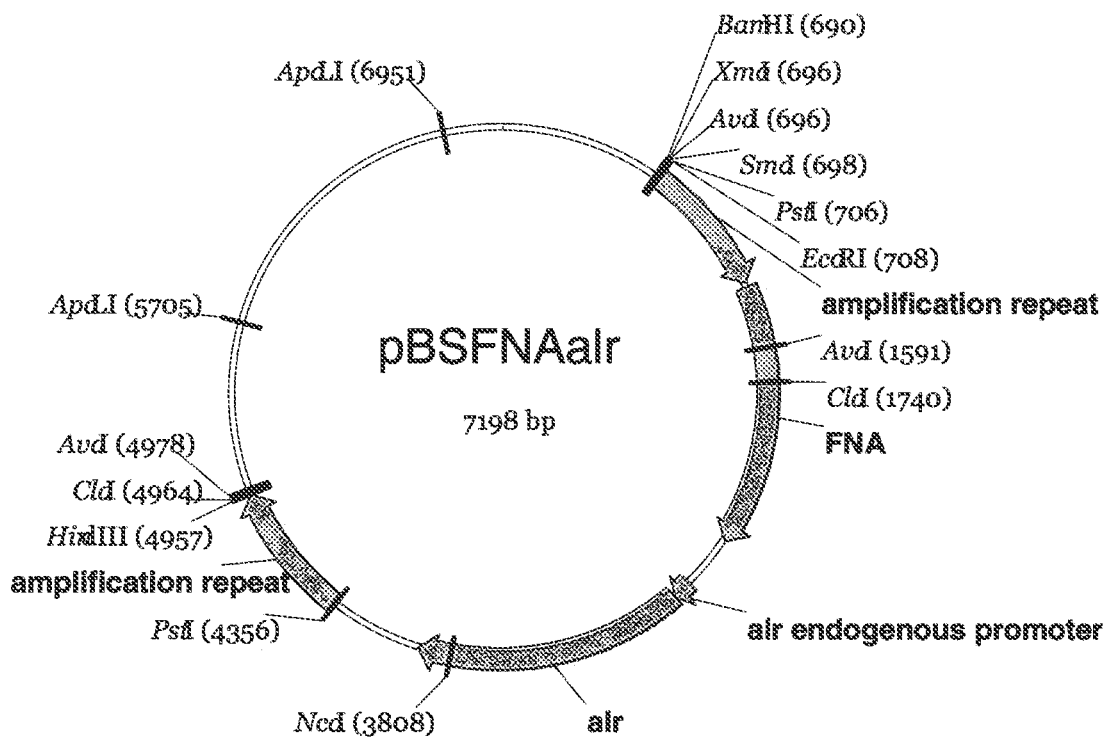
FIG. 2 shows the map of the pBSFNAalr plasmid (SEQ ID NO:2)

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

The term "recombinant" refers to a polynucleotide or polypeptide that does not naturally occur in a host cell. A recombinant molecule may contain two or more naturally-occurring sequences that are linked together in a way that does not occur naturally. A recombinant cell contains a recombinant polynucleotide or polypeptide.

The term "heterologous" refers to elements that are not normally associated with each other. For example, if a host cell produces a heterologous protein, that protein is not normally produced in that host cell. Likewise, a promoter that is operably linked to a heterologous coding sequence is a promoter that is operably linked to a coding sequence that it is not usually operably linked to in a wild-type host cell. The term "homologous", with reference to a polynucleotide or protein, refers to a polynucleotide or protein that occurs naturally in a host cell.

The terms "protein" and "polypeptide" are used interchangeably herein.

A "signal sequence" is a sequence of amino acids present at the N-terminal portion of a protein which facilitates the secretion of the mature form of the protein from the cell. The definition of a signal sequence is a functional one. The mature form of the extracellular protein lacks the signal sequence, which is cleaved off during the secretion process.

The term "nucleic acid" encompasses DNA, RNA, single stranded or double stranded and chemical modifications thereof. The terms "nucleic acid" and "polynucleotide" are used interchangeably herein.

A "vector" refers to a polynucleotide designed to introduce nucleic acids into one or more host cells. In certain embodiments, a vector can autonomously replicate in different host cells and include: cloning vectors, expression vectors, shuttle vectors, plasmids, phage particles, cassettes and the like. In other embodiments, a vector can integrate into a host cell genome.

A "promoter" is a regulatory sequence that initiates transcription of a downstream nucleic acid.

The term "operably linked" refers to an arrangement of elements that allows them to be functionally related. For example, a promoter is operably linked to a coding sequence if it controls the transcription of the sequence.

The term "selective marker" refers to a protein capable of expression in a host that allows for ease of selection of those hosts containing an introduced nucleic acid or vector. Examples of selectable markers include, but are not limited to, antimicrobials (e.g., hygromycin, bleomycin, or chloramphenicol) and/or genes that confer a metabolic advantage, such as a nutritional advantage on the host cell.

The terms "recovered", "isolated", and "separated" as used herein refer to a protein, cell, nucleic acid or amino acid that is removed from at least one component with which it is naturally associated.

As used herein, the terms "transformed", "stably transformed" and "transgenic" used in reference to a cell means the cell has a non-native (e.g., heterologous) nucleic acid sequence integrated into its genome or as an episomal plasmid that is maintained through multiple generations.

As used herein, the term "expression" refers to the process by which a polypeptide is produced based on the nucleic acid sequence of a gene. The process includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed (e.g., transfected mRNA).

The term "hybridization" refers to the process by which a strand of nucleic acid joins with a complementary strand through base pairing as known in the art. A nucleic acid is considered to be "Selectively hybridizable" to a reference nucleic acid sequence if the two sequences specifically hybridize to one another under moderate to high stringency hybridization and wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions include hybridization at about 42 C in 50% formamide, 5×SSC, 5×Denhardt's solution, 0.5% SDS and 100 ug/ml denatured carrier DNA followed by washing two times in 2×SSC and 0.5% SDS at room temperature and two additional times in 0.1×SSC and 0.5% SDS at 42° C.

A "coding sequence" is a DNA segment that encodes a polypeptide.

An "expression cassette" as used herein means a DNA construct comprising a protein-coding region that is operably linked to a suitable control sequence that is capable of effecting expression of the protein in a suitable host cell. Such control sequences may include a promoter to effect transcription, an optional operator sequence to control transcription to produce mRNA, a sequence encoding suitable ribosome binding sites on the mRNA, and enhancers and other sequences which control termination of transcription and translation.

A polypeptide or polynucleotide that is "native to the host cell" has an amino acid or nucleotide sequence that is the same as that of a polypeptide or polynucleotide that is present in an unaltered host cell. In certain instances, a cell may contain a recombinant nucleic acid containing a polynucleotide (e.g., a coding sequence) that is native to the cell. In these instances, the cell contains a recombinant nucleic acid comprising a polynucleotide having a nucleotide sequence that is also present in an unaltered version of the host cell (i.e., a host cell that does not contain any gene knockouts), at a different locus. In certain instances, a cell may contain a recombinant nucleic acid encoding a polypeptide that is native to the cell. In these instances, the cell contains a recombinant nucleic acid encoding a polypeptide having an amino acid sequence that is the same as that of a polypeptide found in an unaltered version of the host cell (i.e., a host cell that does not contain any gene knockouts). The term "endogenous" is synonymous with the term "native".

A "native promoter", with reference to a coding sequence that is operably linked to its native promoter, refers to a promoter of a wild type host cell that is operably linked to the coding sequence in that cell.

The term "direct repeats" refers to at least two sequence elements that are present in the same orientation and that can undergo homologous recombination in a cell. Direct repeats have identical or almost identical nucleotide sequences (e.g., at least 98% or 99% sequence identity) over at least 50 nucleotides, e.g., at least 100, at least 200 or at least 500 or more nucleotides.

The term "inhibitor" refers to a compound that reversibly inhibits an enzyme, either by competitive inhibition or non-competitive inhibition (e.g., allosterically).

The term "essential enzyme" is an enzyme that is essential for the growth of a cell.

The term "expression cassette that provides for significant expression of an essential enzyme", refers to an expression cassette that provides for expression of the essential enzyme at a level that is more than 50% (e.g., at least 70%, at least 90% or at least 100%, up to 1000%) of the level of an endogenous essential enzyme, if the gene for the endogenous essential enzyme is wild-type (i.e., not inactivated) in the cell.

The term "alanine racemase" refers to the enzyme that catalyzes the interconversion of L-alanine and D-alanine. An alanine racemase has an activity described as EC 5.1.1.1, according to IUBMB enzyme nomenclature. The gene encoding an alanine racemase may be denoted as an "alr", "alrA" or "dal" gene.

Other definitions of terms may appear throughout the specification.

DETAILED DESCRIPTION OF EXEMPLARY EMBODIMENTS

As noted above, a method of amplifying a genomic locus is provided. Several general features of the instant method are illustrated in FIG. 1. With reference to FIG. 1, the bacterial host cells employed in the method may comprise a genomic locus comprising an amplification unit of the structure: $A_1$-P-M-$A_2$, where $A_1$ and $A_2$ are direct repeats, P comprises a coding sequence for a polypeptide of interest, and M comprises a coding sequence for an enzyme that is essential to the cell. The formula $A_1$-P-M-$A_2$ is intended to encompass genomic loci that contain direct repeats that are orientated in either direction with respect to P and M.

The amplification unit provides for expression of the polypeptide of interest and the essential enzyme in the cell. In certain cases, region P and region M may independently comprise an expression cassette (i.e., a coding sequence operably linked to a promoter) for the polypeptide of interest and the essential enzyme, respectively. In some embodiments, the amplification unit comprises a first expression cassette for expressing the polypeptide of interest, and a second cassette for expressing the essential enzyme. In other embodiments, the coding sequence of region P may be operably linked to a promoter that is present in the adjacent direct repeat In this embodiment and as will be discussed in greater detail below, the combined nucleotide sequence of the direct repeat and coding sequence for the essential enzyme may be endogenous to the cell, i.e., found in the genome of the host cell. In a particular embodiment, the promoter operably linked to the coding sequence of region M may be endogenous or non-endogenous to that coding sequence. In a particular embodiment, the coding sequence of region M may be driven by the promoter operably linked to the coding sequence of P.

As would be readily apparent, the orientation of P and M in any of the nucleic acids described herein may be in the opposite orientation (i.e., $A_1$-M-P-$A_2$). In this opposite orientation and in certain embodiments, region M's coding sequence may be operably linked to a promoter in direct repeat $A_1$. Alternatively, region M's coding sequence may be operably linked to a promoter that is present in region M.

A population of such cells is contacted with the inhibitor of the essential enzyme, and cells that are resistant to the inhibitor (i.e., cells that can grow and divide in the presence of the inhibitor to form colonies) are selected. As shown in FIG. 1, selected cells have a genomic locus containing multiple copies of the amplification unit, which genomic locus can be described by the formula $(A_1$-P-M$)_n$-$A_2$, where $A_1$ and $A_2$ are direct repeats, and n is at least 2. n may be, for example, 2, 3, 4, 5, 6, 7, 8, 9, 10, or at least 10, e.g., in the range of 10 to 50, or 50 to 100, or more. The selected cells do not have a mutation in the coding sequence of the essential enzyme (e.g., at the binding site of the inhibitor) or in the promoter linked to the coding sequence, relative to non-selected cells. Rather, the selected cells have an increase in copy number of the amplification unit, which allows the cells to grow in the presence of the inhibitor. In certain cases, the population of cells may be subjected to several rounds of selection, with each round of selection using a successively increasing concentration of inhibitor (e.g., a successive doubling in the concentration of inhibitor). In some embodiments, the A1-P-M-A2 amplification unit comprises the polynucleotide sequence set forth in SEQ ID NO:7

```
                                         (SEQ ID NO: 7)
tccattttcttctgctatcaaaataacagactcgtgattttccaaacgag ctttcaaaaagcctctgccccttgcaaatcggatgcctgtctataaaatt cccgatattggttaaacagcggcgcaatggcggccgcatctgatgtctttg cttggcgaatgttcatcttatttcttcctccctctcaataattttttcatt ctatcccttttctgtaaagtttattttttcagaatacttttatcatcatgct ttgaaaaaatatcacgataatatccattgttctcacggaagcacacgcagg tcatttgaacgaattttttcgacaggaatttgccgggactcaggagcattt aacctaaaaaagcatgacatttcagcataatgaacatttactcatgtctat tttcgttcttttctgtatgaaaatagttatttcgagtctctacggaaatag cgagagatgatatacctaaatagagataaaatcatctcaaaaaaatgGGTC TActaaaatattattccaTTTATTacaataaattcacagaatagtctttta agtaagtctactctgaattttttttaaaaggagagggtaaagagtgagaagc aaaaaattgtggatcagtttgctgtttgctttagcgttaatctttacgatg gcgttcggcagcacatcctctgcccaggcggcagggaaatcaaacggggaa aagaaatatattgtcgggtttaaacagacaatgagcacgatgagcgccgct aagaagaaagatgtcatttctgaaaaaggcgggaaagtgcaaaagcaattc aaatatgtagacgcagcttcagctacattaaacgaaaaagctgtaaaagaa ttgaaaaaagacccgagcgtcgcttacgttgaagaagatcacgtagcacat gcgtacgcgcagtccgtgccttacggcgtatcacaaattaaagccctgct
```

-continued

```
ctgcactctcaaggctacactggatcaaatgttaaagtagcggttatcgac agcggtatcgattcttctcatcctgatttaaaggtagcaggcggagccagc atggttccttctgaaacaaatcctttccaagacaacaactctcacggaact cacgttgccggcacagttgcggctcttaataactcaatcggtgtattaggc gttgcgccaagcgcatcactttacgctgtaaaagttctcggtgctgacggt tccggccaatacagctggatcattaacggaatcgagtgggcgatcgcaaac aatatggacgttattaacatgagcctcggcggaccttctggttctgctgct ttaaaagcggcagttgataaagccgttgcatccggcgtcgtagtcgttgcg gcagccggtaacgaaggcacttccggcagctcaagcacagtgggctaccct ggtaaataccccttctgtcattgcagtaggcgctgttgacagcagcaaccaa agagcatctttctcaagcgtaggacctgagcttgatgtcatggcacctggc gtatctatccaaagcacgcttcctggaaacaaatacggcgcgttgaacggt acatcaatggcatctccgcacgttgccggagcggctgattgattattctaa gcacccgaactggacaaacactcaagtccgcagcagtttagaaaacaccac tacaaaacttggtgattattctactatggaaaagggctgatcaacgtacag gcggcagctcagtaaaacataaaaaaccggccttggccccgccggttttttt attattttttcttcctccgcatgttcaatccgctccataatcgacggatggc tccctctgaaaattttaacgagaaacggcgggttgacccggctcagtcccg taacggccaagtcctgaaacgtctcaatcgccgcttcccggtttccggtca gctcaatgccgtaacggtcggcggcgttttcctgataccgggagacttttc gttagacatcgtttcccttttagccatttaattttagtatgatatgtaaatg atattgaataaaagctaggaagtgtcgtaatgagcacaaaacctttttaca gagatacgtgggcggaaattgacttgtccgcgataaaggaaaatgtcagca atatgaaaaacatatcggtgaacatgtccacttgatggcagttgtgaaag caaacgcctacgggcatggtgatgcagaaacagcaaaggctgctcttgacg caggtgcttcatgcttggccgtggccatttttggatgaagcgatttcactgc gcaaaaagggattgaaggcgcctatattggtgcttggcgcggttcccccgg agtatgtggcaatcgctgctgagtatgacgtgaccttaacaggttattctg ttgaatggcttcaggaggcagcccgccacacgaaaaaaggttctcttcatt ttcatctgaaggtcgatacggggatgaacagacttggtgtaaaaacagagg aagaagttcagaacgtgatggcaattcttgaccgcaaccctcgtttaaagt gcaaaggggtatttacccatttttgcgacagcggatgaaaagaaagaggct atttcttaatgcagtttgagcgctttaaagagctgattgctccgctgccgt taaagaatctaatggtccactgcgcgaacagcgccgctggactccggctga aaaaaggctttttttaatgcagtcagattcggcatcggcatgtatggccttc gcccgtctgctgacatgtcggacgagataccgtttcagctgcgtccggcat ttaccctgcattcgacactgtcacatgtcaaactgatcagaaaaggcgaga gcgtcagctacggagccgagtacacagcggaaaaagacacatggatcggga cggtgcctgtaggctatgcggacggctggctccgaaaattgaaagggaccg acatccttgtgaagggaaaacgcctgaaaattgccggccgaatttgcatgg
```

-continued

```
accaatttatggtggagctggatcaggaatatccgccgggcacaaaagtca
cattaataggccggcagggggatgaatatatttccatggatgagattgcag
gaaggctcgaaaccattaactatgaggtggcctgtacaataagttcccgtg
ttccccgtatgttttggaaaatgggagtataatggaagtaagaaatcctt
tattgcaggtaaatataagcaattaacctaatgactggcttttataatatg
agataatgccgactgtacttttacagtcggttttctaatgtcactaacct
gccccgttagttgaagaaggttttatattacagctccagatccatatcct
tcttttctgaaccgacttctccttttcgcttctttattccaattgattt
attgacgttgagcctcggaaccctttaacaatcccaaaacttgtcgaatggt
cggcttaatagctcacgctatgccgacattcgtctgcaagatttgttaagg
gttcttctcaacgcacaataaattttctcggcataaatgcgtggtctaatt
tttattttaataaccttgatagcaaaaaatgccattccaatacaaaacca
catacctataatcgacctgcaggaattaattcctccattttcttctgctat
caaaataacagactcgtgattttccaaacgagctttcaaaaaagcctctgc
cccttgcaaatcggatgcctgtctataaaattcccgatattggcttaaaca
gcggcgcaatggcggccgcatctgatgtctttgcttggcgaatgttcatct
tatttcttcctccctctcaataattttttcattctatccttttctgtaaa
gtttatttttcagaatacttttatcatcatgctttgaaaaaatatcacgat
aatatccattgttctcacggaagcacacgcaggtcatttgaacgaatttt
tcgacaggaatttgccgggactcaggagcatttaacctaaaaaagcatgac
atttcagcataatgaacatttactcatgtctattttcgttcttttctgtat
gaaaatagttatttcgagtctctacggaaatagcgagagatgatataccta
aatagagataaaatcatctcaaaaaaatgGGTCTActaaaatattattcca
TTTATTacaataaattcacagaatagtcttttaagtaagtctactctgaat
tttttta
``` wherein repeat units A1 and A2 are shown underlined, the polynucleotide sequence encoding the protein of interest i.e. the subtilisin FNA, is shown in bolded letters, and the polynucleotide sequence encoding the essential enzyme e.g. alanine racemase, is shown in italics. Promoter sequences are shown in bolded capital letters.

Since the host cells made by the method contain more copies of the first expression cassette, the cells may produce more polypeptide of interest encoded by the first expression cassette than host cells that have a single copy of the $A_1$-P-M-$A_2$ amplification unit. In particular embodiments, the resultant host cells may produce at least 20%, at least 40% at least 60%, at least 80% at least 100%, at least twice, at least three times, at least four times, at least five times or at least 10 times, up to about 100 times more protein as compared to otherwise identical host cells that have a single copy of the $A_1$-P-M-$A_2$ amplification unit.

The concentration of the inhibitor employed in the subject methods may vary with the essential enzyme used and the potency of the inhibitor. In particular embodiments, the inhibitor may be at a concentration in the range of 1 µM to 100 mM, e.g., in the range of 5 µM to 10 mM, 20 µM to 1 mM, although inhibitor concentrations outside of these ranges are envisioned. The inhibitor may be added to a liquid culture, or may be present in solid media (e.g., agar media) upon which the bacteria are grown. As noted above, the population of cells may be subjected to several rounds of selection, with each round of selection using a successively increasing concentration of inhibitor (e.g., a successive doubling in the concentration of inhibitor).

In a particular embodiment, the amplification unit does not contain an antibiotic resistance marker, and cell selection may be done in an antibiotic-free medium.

The first and second expression cassettes, and the host cells, are described in greater detail below.

Expression Cassettes

As noted above, the amplification unit provides for expression of the polypeptide of interest and of the essential enzyme. As such, the amplification unit generally contains at least two expression cassettes: a first expression cassette for the expression of the polypeptide of interest, and a second expression cassette for the expression of the essential gene. Each expression cassette contains, in operable linkage: a promoter, a coding sequence, and a terminator. In certain cases, region P of the amplification unit may comprise the first expression cassette and region M of the amplification unit may comprise the second expression cassette. In other cases and as noted above, the direct repeat adjacent to region P may contain a promoter operably linked to the coding sequence of region P. In certain cases, the contiguous nucleotide sequence of region P and the direct repeat adjacent to region P may be endogenous to the host cell (i.e., present in the genome of the host cell). In a particular embodiment, the coding sequence of region M may be operably linked to a promoter of region P.

Each expression cassette discussed herein may contain the following elements in operable linkage: a promoter, a coding sequence, and a terminator sequence, where the expression cassette is sufficient for the production of the protein in the host cell. As will be discussed in greater detail below, the coding sequence of the first expression cassette may encode a recombinant protein, e.g., a therapeutic protein or so-called "industrial enzyme". In particular embodiments, this coding sequence may encode a protein having a signal sequence that provides for secretion of the protein from the cell. As noted above and as will be described in greater detail below, the second expression cassette provides for expression of an essential enzyme.

The choice of promoters, terminators and signal sequence, if used, largely depends on the host cell used. Host cells include *Bacillus* sp. host cell, *Streptomyces* sp. host cells, *E. coli*, and other bacterial host cells. As noted above, in exemplary embodiments, a *Streptomyces* host cell may employed, in which case the signal sequence, if used, may be a celA signal sequence. In certain cases, the celA signal sequence may be the signal sequence encoded by the *S. lividans* cellulase A gene, CelA, as described by Kluepfel et al. (Nature Biotechnol. 1996 14:756-759). In other exemplary embodiments in which a *Bacillus* host cell is employed, the signal sequence may be any sequence of amino acids that is capable of directing the fusion protein into the secretory pathway of the *Bacillus* host cell. In certain cases, signal sequences that may be employed include the signal sequences of proteins that are secreted from wild-type *Bacillus* cells. Such signal sequences include the signal sequences encoded by α-amylase, protease, e.g., aprE or subtilisin E, or β-lactamase genes. Exemplary signal sequences include, but are not limited to, the signal sequences encoded by an α-amylase gene, a subtilisin gene, a β-lactamase gene, a neutral protease gene (e.g., nprT, nprS, nprM), or a prsA gene from any suitable *Bacillus* species, including, but not limited to, *B. stearothermophilus*, *B. licheniformis*, *B. clausii*, *B. subtilis* and *B. amyloliquefa*-

*ciens*. In one embodiment, the signal sequence is encoded by the aprE gene of *B. subtilis* (as described in Appl. Microbiol. Biotechnol. 2003 62:369-73). Further signal peptides are described by Simonen and Palva (Microbiological Reviews 1993 57: 109-137), and other references.

Suitable promoters and terminators for use in *Bacillus* and *Streptomyces* host cells are known and include: the promoters and terminators of apr (alkaline protease), npr (neutral protease), amy (α-amylase) and β-lactamase genes, as well as the *B. subtilis* levansucrase gene (sacB), *B. licheniformis* alpha-amylase gene (amyL), *B. stearothermophilus* maltogenic amylase gene (amyM), *B. amyloliquefaciens* alpha-amylase gene (amyQ), *B. licheniformis* penicillinase gene (penP), *B. subtilis* xylA and xylB genes, the promoters and terminators described in WO 93/10249, WO 98/07846, and WO 99/43835. Expression cassettes for use in *Streptomyces* host cells can be constructed using the promoters and terminators described in Hopwood et al (Genetic Manipulation of *Streptomyces*: A Laboratory Manual; Cold Spring Harbor Laboratories, 1985), Hopwood et al (Regulation of Gene Expression in Antibiotic-producing *Streptomyces*. In Booth, I. and Higgins, C. (Eds) Symposium of the Society for General Microbiology, Regulation of Gene Expression, Cambridge University Press, 1986 pgs. 251-276), Formwald et al (Proc. Natl. Acad. Sci. 1987 84: 2130-2134), Pulido et al (Gene. 1987 56:277-82); Dehottay et al (Eur. J. Biochem. 1987 166:345-50), Taguchi (Gene. 1989 84:279-86), Schmitt-John et al (Appl. Microbiol. Biotechnol. 1992 36:493-8), Motamedi (Gene 1995 160:25-31) and Binnie (Protein Expr. Purif. 1997 11:271-8), for example. In one embodiment, the A4 promoter may be employed, which promoter is described in WO 06/054997, which is incorporated by reference herein.

In certain embodiments, either of the coding sequences may be codon optimized for expression of the polypeptide of interest in the host cell used. Since codon usage tables listing the usage of each codon in many cells are known in the art (see, e.g., Nakamura et al, Nucl. Acids Res. 2000 28: 292) or readily derivable, such nucleic acids can be readily designed giving the amino acid sequence of the proteins to be expressed.

Systems for expression of recombinant proteins in *Streptomyces* and *Bacillus* host cells are well known in the art and need not be discussed in any greater detail than that set forth above.

First Expression Cassette

A first expression may comprise a promoter and a polynucleotide encoding a protein of interest (i.e., a coding sequence), where the promoter and the polynucleotide are operably linked such that the isolated nucleic acid causes transcription of the polynucleotide and production of the protein of interest.

The encoded protein of interest may be a so called "industrial enzyme", a therapeutic protein, a reporter protein, a food additive or a foodstuff or the like. In one embodiment, the protein of interest may be an enzyme such as a carbohydrase, such as a liquefying and saccharifying α-amylase, an alkaline α-amylase, a β-amylase, a cellulase; a dextranase, an α-glucosidase, an α-galactosidase, a glucoamylase, a hemicellulase, a pentosanase, a xylanase, an invertase, a lactase, a naringanase, a pectinase or a pullulanase; a protease such as an acid protease, an alkali protease, bromelain, ficin, a neutral protease, papain, pepsin, a peptidase, rennet, rennin, chymosin, subtilisin, thermolysin, an aspartic proteinase, or trypsin; a lipase or esterase, such as a triglyceridase, a phospholipase, a pregastric esterase, a phosphatase, a phytase, an amidase, an iminoacylase, a glutaminase, a lysozyme, or a penicillin acylase; an isomerase such as glucose isomerase; an oxidoreductase, e.g., an amino acid oxidase, a catalase, a chloroperoxidase, a glucose oxidase, a hydroxysteroid dehydrogenase or a peroxidase; a lyase such as an acetolactate decarboxylase, an aspartic β-decarboxylase, a fumarase or a histadase; a transferase such as cyclodextrin glycosyltranferase; or a ligase, for example. In particular embodiments, the protein may be an aminopeptidase, a carboxypeptidase, a chitinase, a cutinase, a deoxyribonuclease, an α-galactosidase, a β-galactosidase, a β-glucosidase, a laccase, a mannosidase, a mutanase, a pectinolytic enzyme, a polyphenoloxidase, ribonuclease or transglutaminase, for example. In particular embodiments, the protein of interest encoded by the first expression cassette is a detergent-additive protein, i.e., a protein (e.g., an enzyme) that is: a) secreted from the cell and b) to be added to laundry detergent. Exemplary detergent-additive proteins include proteases, e.g., subtilisins, α-amylases and lipases. Subtilisins, i.e., extracellular alkaline serine proteases, are of particular interest. A subtilisin may have an amino acid sequence that is found in a wild type genome (i.e., the subtilisin may be a naturally-occurring subtilisin) or may be a variant of a naturally-occurring subtilisin and thus may contain an amino acid sequence that is at least 80%, at least 90%, at least 95% or at least 98% identical to a subtilisin encoded by a wild-type genome. Exemplary subtilisins include: Alcanase® (Novozymes), FNA™ (Genencor), Savinase® (Novozymes), Purafect™ (Genencor), KAP™ (Kao), Everlase™ (Novozymes), Purafect OxP™ (Genencor), FN4™ (Genencor), BLAP S™ (Henkel), BLAP X™ (Henkel), Esperase® (Novozymes), Kannase™ (Novozymes) and Prosperase™ (Genencor). In other embodiments, the subtilisin may be subtilisin 168, subtilisin BPN', subtilisin Carlsberg, subtilisin DY, subtilisin 147 or subtilisin 309 (See e.g., EP414279B, WO89/06279 and Stahl et al., J. Bacteriol. 1984 159:811-818). In some embodiments, the subtilisin encoded by the first expression cassette is FNA *VRSKKLWISLLFALALIFTMAFGST-SSAQAAGKSNGEKKYIVGFKQTMSTMSAAKKKDVI SEKGGKVQKQFKYVDAASATLNEKAVKELKKDPS-VAYVEEDHVAHA YAQSVPYGVSQ IKAPALHSQ-GYTGSNVKVAVIDSGIDSSHPDLKVAGGASMVPSET-NPFQDNNS* HGTHVAGTVAALNNSIGVLGVAPSASLYAVKVL-GADGSGQYSWIINGIEWAIA NNMDVINMSLG-GPSGSAALKAAVDKAVASGV-VVVAAAGNEGTSGSSSTVGYP GKYPSVIAVGAVDSSNQRASFSSVGPELDVMAPGV-SIQSTLPGNKYGALNGTS MASPHVAGAAALILSKHP-NWTNTQVRSSLENTTTKLGDSFYYGKGLINVQAA AQ (SEQ ID NO:8). The pre-pro region of the subtilisin is shown in italics, and the mature region is shown in bolded letters (SEQ ID NO:12). An example of a polynucleotide that encodes FNA is:

```
                                        (SEQ ID NO: 9)
gtgagaagcaaaaaattgtggatcagtagctgatgattagcgttaata ttacgatggcgttcggcagcacatcctctgcccaggcggcagggaaat caaacggggaaaagaaatatattgtcgggataaacagacaatgagcac gatgagcgccgctaagagaaagatgtcatactgaaaaaggcgggaaag tgcaaaagcaattcaaatatgtagacgcagcttcagctacattaaacg aaaaagctgtaaaagaattgaaaaaagacccgagcgtcgcttacgttg
```

-continued

```
aagaagatcacgtagcacatgcgtacgcgcagtccgtgccttacggcg tatcacaaattaaagcccctgctctgcactctcaaggctacactggat caaatgttaaagtagcggttatcgacagcggtatcgattcactctcct gatttaaaggtagcaggcggagccagcatggaccactgaaacaaatca ttccaagacaacaactctcacggaactcacgttgccggcacagagcgg ctcttaataactcaatcggtgtattaggcgttgcgccaagcgcatcac tttacgctgtaaaagactcggtgctgacggaccggccaatacagctgg atcattaacggaatcgagtgggcgatcgcaaacaatatggacgttatt aacatgagcctcggcggaccttctggttctgctgctttaaaagcggca gttgataaagccgttgcatccggcgtcgtagtcgttgcggcagccggt aacgaaggcacttccggcagctcaagcacagtgggctaccctggtaaa tacccactgtcattgcagtaggcgctgagacagcagcaaccaaagagc atctttctcaagcgtaggacctgagcttgatgtcatggcacctggcgt atctatccaaagcacgcttcctggaaacaaatacggcgcgttgaacgg tacatcaatggcatctccgcacgagccggagcggctgattgattattc taagcacccgaactggacaaacactcaagtccgcagcagatagaaaac accactacaaaacttggtgattctactactatggaaaagggctgatca acgtacaggcggcagctcagtaa.
```

Exemplary subtilisins and other proteases that may be employed herein include those described in WO 99/20770; WO 99/20726; WO 99/20769; WO 89/06279; RE 34,606; U.S. Pat. No. 4,914,031; U.S. Pat. No. 4,980,288; U.S. Pat. No. 5,208,158; U.S. Pat. No. 5,310,675; U.S. Pat. No. 5,336,611; U.S. Pat. No. 5,399,283; U.S. Pat. No. 5,441,882; U.S. Pat. No. 5,482,849; U.S. Pat. No. 5,631,217; U.S. Pat. No. 5,665,587; U.S. Pat. No. 5,700,676; U.S. Pat. No. 5,741,694; U.S. Pat. No. 5,858,757; U.S. Pat. No. 5,880,080; U.S. Pat. No. 6,197,567; and U.S. Pat. No. 6,218,165. Subtilisins in general are reviewed in great detail in Siezen (Protein Sci. 1997 6:501-523), and detergent-additive subtilisins are reviewed in Bryan (Biochim Biophys. Acta 2000 1543:203-222), Maurer (Current Opinion in Biotechnology 2004 15:330-334) and Gupta (Appl Microbiol Biotechnol. 2002 59:15-32). Certain subtilisins of interest have an activity described as EC 3.4.4.16, according to IUBMB enzyme nomenclature.

In other embodiments, the protein of interest may be a therapeutic protein (i.e., a protein having a therapeutic biological activity). Examples of suitable therapeutic proteins include: erythropoietin, cytokines such as interferon-α, interferon-β, interferon-γ, interferon-o, and granulocyte-CSF, GM-CSF, coagulation factors such as factor VIII, factor IX, and human protein C, antithrombin III, thrombin, soluble IgE receptor α-chain, IgG, IgG fragments, IgG fusions, IgM, IgA, interleukins, urokinase, chymase, and urea trypsin inhibitor, IGF-binding protein, epidermal growth factor, growth hormone-releasing factor, annexin V fusion protein, angiostatin, vascular endothelial growth factor-2, myeloid progenitor inhibitory factor-1, osteoprotegerin, α-1-antitrypsin, α-feto proteins, DNase II, kringle 3 of human plasminogen, glucocerebrosidase, TNF binding protein 1, follicle stimulating hormone, cytotoxic T lymphocyte associated antigen 4-Ig, transmembrane activator and calcium modulator and cyclophilin ligand, soluble TNF receptor Fc fusion, glucagon like protein 1 and IL-2 receptor agonist. Antibody proteins, e.g., monoclonal antibodies that may be humanized, are of particular interest.

In a further embodiment, the protein of interest may be a reporter protein. Such reporter proteins may be optically detectable or colorigenic, for example. In this embodiment, the protein may be a β-galactosidase (lacZ), β-glucuronidase (GUS), luciferase, alkaline phosphatase, nopaline synthase (NOS), chloramphenicol acetyltransferase (CAT), horseradish peroxidase (HRP) or a fluorescent protein, e.g., green fluorescent protein (GFP), or a derivative thereof.

As noted above, the coding sequence may encode a fusion protein. In some of these embodiments, the fusion protein may provide for secretion of the protein of interest from the host cell in which it is expressed and, as such, may contain a signal sequence operably linked to the N-terminus of the protein of interest, where the signal sequence contains a sequence of amino acids that directs the protein to the secretory system of the host cell, resulting in secretion of the protein from the host cell into the medium in which the host cell is growing. The signal sequence is cleaved from the fusion protein prior to secretion of the protein of interest.

Second Expression Cassette

The second expression cassette provides for expression of an essential enzyme where, as noted above, an essential enzyme is required by the cell for cell growth. In particular embodiments, the essential enzyme may be conditionally essential in that it is required for cell growth only under certain conditions (e.g., in the absence of an exogenous compound that negates any loss of the essential enzyme). In certain cases, cells lacking activity of a conditionally essential enzyme (which may be made by inactivating the gene encoding the enzyme, or by contacting the cells with an inhibitor of the enzyme) may be grown in culture by adding an exogenous compound, which in certain cases may be a product of the enzyme or alternative carbon source. Thus, in certain cases, the essential enzyme employed in the second expression cassette may be an enzyme that, when absent from a cell, renders the cell auxotrophic for a specific compound or unable to utilize one or more specific carbon sources.

Examples of such essential enzyme/inhibitor combinations are known and include, for example: enzymes that are involved in amino acid synthesis and their respective inhibitors; and enzymes involved in utilization of a specific carbon source, and their respective inhibitors. Examples of such enzymes/inhibitors combinations are set forth below. Inactivation of a gene encoding an enzyme involved in the synthesis of an amino acid causes auxotrophy for that amino acid. Likewise, inactivation of a gene encoding an enzyme involved in the utilization of a specific carbon source causes auxotrophy for another carbon source. The enzyme does not cleave the inhibitor. Rather, the inhibitor reversibly and specifically inhibits the catalytic activity of the enzyme, either competitively or non-competitively.

In one embodiment, the enzyme may be S-adenosylmethionine synthetase (encoded by metE; Genbank accession no. U52812; see Yocum et al, *Cloning and characterization of the metE gene encoding S-adenosylmethionine synthetase from Bacillus subtilis*. J. Bacteriol. 1996 178: 4604) which can be inhibited by cycloleucine (Chiang et al *Molecular characterization of Plasmodium falciparum S-adenosylmethionine synthetase*. Biochem J. 1999 344: 571-6) as well as methionine analogs, purine analogs, 8-azaguanine and azathioprine (Berger et al *Characterisation of methionine adenosyltransferase from Mycobacterium smegmatis and M. tuberculosis* BMC Microbiol. 2003; 3: 12).

Inactivation of the S-adenosyl-methionine synthetase gene causes methionine auxotrophy.

In another embodiment, the enzyme may be 3-isopropylmalate dehydrogenase, which catalyzes the conversion of 3-carboxy-2-hydroxy-4-methylpentanoate to 3-carboxy-4-methyl-2-oxopentanoate. This enzyme is encoded by leuB, and leuB-deficient strains are leucine auxotrophs. 3-isopropylmalate dehydrogenase can be inhibited by, for example, O-isobutenyl oxalylhydroxamate (Singh et al The High-resolution Structure of LeuB (Rv2995c) from *Mycobacterium tuberculosis* Journal of Molecular Biology 2005 346: Pages 1-11).

In another embodiment, the enzyme may be diaminopimelate decarboxylase, which catalyses the conversion of Meso-2,6-diaminoheptanedioate to L-lysine and is encoded by lysA. A lysA-deficient strain will be a lysine auxotroph Inhibitors of diaminopimelate decarboxylase include analogs of diaminopimelic acid including, but not limited to: Lanthionine sulfoxides, meso and LL-isomers of lanthionine sulfone, lanthionine, N-modified analogs including N-hydroxydiaminopimelate 4 and N-aminodiaminopimelate 5 (see Kelland et al J. Biol. Chem. 1986 *Analogs of diaminopimelic acid as inhibitors of meso-diaminopimelate decarboxylase from Bacillus sphaericus and wheat germ* 261: 13216-13223).

In another embodiment, the enzyme may be glutamyl-tRNA reductase, which catalyses the synthesis of 5-amino levulinic acid and is encoded by hemA. A hemA-deficient strain is auxotrophic for 5-amino levulinic acid or haemin. This enzyme can be inhibited by glutamycin (Schauer et al *Escherichia coli* Glutamyl-tRNA Reductase J. Biol. Chem. 2002 277: 48657-48663).

In a further embodiment, the enzyme may be D-alanine racemase, which catalyzes the interconversion of L-alanine and D-alanine and is encoded by alr (also known as dal). An alr deficient strain is auxotrophic for D-alanine, which is required for cell wall biosynthesis Inhibitors of D-alanine racemase include, but are not limited to, D-cycloserine, β-chloro-D-alanine and O-carbamyl-D-serine (see, e.g., Manning et al, Inhibition of Bacterial Growth by β-chloro-D-alanine PNAS1974 71: 417-421). In some embodiments, the second expression cassette comprises a polynucleotide e.g. atgagcac aaaaccttt tacagagata cgtgggcgga aattgacttg tccgcgataa aggaaaatgt cagcaatatg aaaaaacata tcggtgaaca tgtccacttg atggcagttg tgaaagcaaa cgcctacggg catggtgatg cagaaacagc aaaggctgct cttgacgcag gtgcttcatg cttggccgtg gccattttgg atgaagcgat ttcactgcgc aaaaagggat tgaaggcgcc tatattggtg cttggcgcgg ttcccccgga gtatgtggca atcgctgctg agtatgacgt gaccttaaca ggttattctg ttgaatggct tcaggaggca gcccgccaca cgaaaaaagg ttctcttcat tttcatctga aggtcgatac ggggatgaac agacttggtg taaaaacaga ggaagaagtt cagaacgtga tggcaattct tgaccgcaac cctcgtttaa agtgcaaagg ggtatttacc cattttgcga cagcggatga aaaagaaaga ggctatttct taatgcagtt tgagcgcttt aaagagctga ttgctccgct gccgttaaag aatctaatgg tccactgcgc gaacagcgcc gctggactcc ggctgaaaaa aggctttttt aatgcagtca gatcggcat cggcatgtat ggccttcgcc cgtctgctga catgtcggac gagataccgt ttcagctgcg tccggcattt accctgcatt cgacactgtc acatgtcaaa ctgatcagaa aaggcgagag cgtcagctac ggagccgagt acacagcgga aaaagacaca tggatcggga cggtgcctgt aggctatgcg gacggctggc tccgaaaatt gaaagggacc gacatccttg tgaaggaaa acgcctgaaa att gccggcc gaatttgcat ggaccaattt atggtggagc tggatcagga atatcgccg ggcacaaaag tcacattaat aggccggcag gggatgaat atatttcat ggatgagatt gcaggaaggc tcgaaaccat taactatgag gtggcctgta caataagttc ccgtgttccc cgtatgtttt tggaaaatgg gagtataatg gaag taagaa atcctttatt gcaggtaaat ataagcaatt aa (SEQ ID NO:10), which encodes D-alanine racemase MSTKPFYRDT-WAEIDLS AIKENVSNMKKHIGEHVHLMAVVKA-NAYGHGDAETAK AALDAGASCLAVAILDEAISLRK-KGLKAPILVLGAVPPEYVAIAAEYDVTLTGYSV EWLQEAARHTKKGSLHFHLKVDTGMNRLGVK-TEEEVQNVMAILDRNPRLKCKG VFTHFATADEKER-GYFLMQFERFKELIAPLPLKNLMVHCANSAAGLR-LKKGFFNA VRFGIGMYGLRPSADMSDEIPFQLRPAFTLH-STLSHVKLIRKGESVSYGAEYTAEK DTWIGTVPVG-YADGWLRKLKGTDILVKGKRLKIAGRICMDQFM-VELDQEYPPGT KVTLIGRQGDEYISMDEIAGRLETINYEVACTISS-RVPRMFLENGSIMEVRNPLLQV NISN (SEQ ID NO:11).

Other essential enzymes for which inhibitors may be used include: xylose isomerase (xylA), gluconate kinase (EC 2.7.1.12), gluconate permease (gntK or gntP), glycerol kinase, glycerol dehydrogenase, e.g., glpP, glpF, glpK, or the glpD or arabinose isomerase (araA), for example.

In particular embodiments, the second expression cassette provides for significant expression of an essential enzyme, in that the essential enzyme is produced at a level that is more than 50% (e.g., at least about 70%, at least about 90% or at least about 100%, up to at least about 1000%) of the level of an endogenous essential enzyme, if the gene for the endogenous essential enzyme is wild-type (i.e., not inactivated) in the cell.

In certain embodiments, the essential enzyme encoded by region M may be naturally-occurring in that it has the amino acid sequence of a wild-type essential enzyme. In other embodiments, the essential enzyme encoded by region M may be a variant of a naturally-occurring enzyme, e.g., may have an amino acid sequence that is at least about 80% identical to, at least about 90% identical to, at least about 95% identical to, at least about 98% identical to, or at least about 99% identical to a naturally occurring essential enzyme.

In particular embodiments, the essential enzyme may have a naturally occurring amino acid sequence and, in certain embodiments, may be endogenous to the host cell in that it has an amino acid sequence that is encoded by the genome of the host cell, prior to any inactivation mutations.

In particular embodiments, nucleotide sequence of the expression cassette (i.e., the promoter, coding sequence and terminator) may be of a gene that is endogenous to the host cell, prior to any inactivating mutations. Such a gene may be at a different genomic locus to the locus of the expression cassettes.

Although not required for practice of the instant method, the endogenous gene for the essential enzyme (i.e., a gene that is present in a host cell that does not yet contain the $A_1$-P-M-$A_2$ locus) may be inactivated by mutation. Methods for specifically inactivating bacterial genes, e.g., by deletion, substitution or insertion, are well known in the art.

Host Cells

The bacterial host cells employed herein may be gram positive or gram negative and include, but are not limited to: *Bacillus* sp. bacteria, e.g., *Bacillus clausii, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis,* or *Bacillus thuringiensis* bacteria; *Streptomyces* sp. bacteria, e.g., *S. lividans, S. carbophilus, S. helvaticus, S. rubiginosus* or *S. murinus* bacteria, *Pseudomonas* sp. bacteria and *E. coli.* In particular cases, the bacterial host cells may be cells of a strain that has a history of use for production of proteins that has GRAS status, i.e., a Generally Recognized as Safe, by the FDA.

*B. subtilis* host cells include but not limited to those described in U.S. Pat. Nos. 5,264,366 and 4,760,025 (RE 34,606), as well as 1A6 (ATCC 39085), 168 (1A01), SB19, W23, Ts85, B637, PB1753 through PB1758, PB3360, JH642, 1A243 (ATCC 39,087), ATCC 21332, ATCC 6051, MI113, DE100 (ATCC 39,094), GX4931, PBT 110, and PEP 211 strain (See e.g., Hoch et al., Genetics 1973 73:215-228; U.S. Pat. No. 4,450,235; U.S. Pat. No. 4,302,544; and EP 0134048). The use of *B. subtilis* as an expression host is also described by Palva et al. and others (See, Palva et al., Gene 1982 19:81-87; also see Fahnestock and Fischer, J. Bacteriol. 1986 165:796-804; and Wang et al., Gene 1988 69:39-47), for example.

In particular embodiments, the *Bacillus* host cell may be engineered to maximize protein expression, and, as such, may contain an inactivating alteration in at least one of the following genes, degU, degS, degR and degQ. See, Msadek et al. (J. Bacteriol. 1990 172:824-834) and Olmos et al, (Mol. Gen. Genet. 1997 253:562-567). One strain is of the species *Bacillus subtilis* and carries a degU32(Hy) mutation. In another embodiment, the *Bacillus* host cell may comprise a mutation or deletion in scoC4, (See, Caldwell et al., J. Bacteriol. 2001 183:7329-7340); spoIIE (See, Arigoni et al., Mol. Microbiol. 1999 31:1407-1415); oppA or another gene in the opp operon (See, Perego et al., Mol. Microbiol. 1991 5:173-185).

The bacterial cells used in the subject method may be made by inserting recombinant nucleic acid into a genome of a bacterial host cell. In particular embodiments, the cells may be made by homologous or non-homologous recombination using a method similar to established methods, such as those of Jung et al (J. Gen. Appl. Microbiol. 1998 44 107-111); Tangney et al (FEMS Microbio. Lett. 1995 125: 107-114); Petit et al (EMBO J. 1992 11:1317-1326); U.S. Pat. No. 5,733,753 and published US patent application 20070134760.

The host cell may or may not have an inactivated endogenous gene encoding the essential enzyme.

Protein Production Methods

Methods of using the above-described cells are also provided. In certain embodiments, the subject methods include: culturing a population of cell to produce the protein of interest encoded by the first expression cassette. In certain embodiments and as discussed above, the protein of interest may be secreted into the culture medium. Particular embodiments of the method include the step of recovering the protein of interest from the culture medium.

The protein of interest may be recovered from growth media by any convenient method, e.g., by precipitation, centrifugation, affinity, filtration or any other method known in the art. For example, affinity chromatography (Tilbeurgh et al., (1984) FEBS Lett. 16:215); ion-exchange chromatographic methods (Goyal et al., (1991) Biores. Technol. 36:37; Fliess et al., (1983) Eur. J. Appl. Microbiol. Biotechnol. 17:314; Bhikhabhai et al., (1984) J. Appl. Biochem. 6:336; and Ellouz et al., (1987) Chromatography 396:307), including ion-exchange using materials with high resolution power (Medve et al., (1998) J. Chromatography A 808:153; hydrophobic interaction chromatography (Tomaz and Queiroz, (1999) J. Chromatography A 865:123; two-phase partitioning (Brumbauer, et al., (1999) Bioseparation 7:287); ethanol precipitation; reverse phase HPLC; chromatography on silica or on a cation-exchange resin such as DEAE; chromatofocusing; SDS-PAGE; ammonium sulfate precipitation; and gel filtration using, e.g., Sephadex G-75, may be employed. In particular embodiments, the detergent-additive protein may be used without purification from the other components the culture medium. In certain embodiments, the components of the culture medium may simply be concentrated, for example, and then used without further purification of the protein from the other components of the growth medium.

In some embodiments, a cell may be cultured under batch or continuous fermentation conditions. Classical batch fermentation methods use a closed system, where the culture medium is made prior to the beginning of the fermentation run, the medium is inoculated with the desired organism(s), and fermentation occurs without the subsequent addition of any components to the medium. In certain cases, the pH and oxygen content, but not the carbon source content, of the growth medium may be altered during batch methods. The metabolites and cell biomass of the batch system change constantly up to the time the fermentation is stopped. In a batch system, cells usually progress through a static lag phase to a high growth log phase and finally to a stationary phase where growth rate is diminished or halted. If untreated, cells in the stationary phase eventually die. In general terms, the cells in log phase produce most protein.

A variation on the standard batch system is the "fed-batch fermentation" system. In this system, nutrients (e.g., a carbon source, nitrogen source, salts, $O_2$, or other nutrient) are only added when their concentration in culture falls below a threshold. Fed-batch systems are useful when catabolite repression is apt to inhibit the metabolism of the cells and where it is desirable to have limited amounts of nutrients in the medium. Measurement of the actual nutrient concentration in fed-batch systems is estimated on the basis of the changes of measurable factors such as pH, dissolved oxygen and the partial pressure of waste gases such as $CO_2$. Batch and fed-batch fermentations are common and known in the art.

Continuous fermentation is an open system where a defined culture medium is added continuously to a bioreactor and an equal amount of conditioned medium is removed simultaneously for processing. Continuous fermentation generally maintains the cultures at a constant high density where cells are primarily in log phase growth.

Continuous fermentation allows for the modulation of one factor or any number of factors that affect cell growth and/or end product concentration. For example, in one embodiment, a limiting nutrient such as the carbon source or nitrogen source is maintained at a fixed rate and all other parameters are allowed to moderate. In other systems, a number of factors affecting growth can be altered continuously while the cell concentration, measured by media turbidity, is kept constant. Continuous systems strive to maintain steady state growth conditions. Thus, cell loss due to medium being drawn off may be balanced against the cell growth rate in the fermentation. Methods of modulating nutrients and growth factors for continuous fermentation processes as well as techniques for maximizing the rate of product formation are known.

EXPERIMENTAL

The following examples are provided in order to demonstrate and further illustrate certain preferred embodiments and aspects of the present invention and are not to be construed as limiting the scope thereof.

Materials and Methods

The experimental techniques used to manipulate DNA were standard techniques within the field of molecular biology (Sambrook et al. Molecular cloning: A Laboratory Manual). Plasmids were prepared and inserts purified using Qiagen kits (Qiagen Inc.). Restriction endonucleases and other enzymes were purchased from Roche Applied Science (Indianapolis, Ind.) and used as recommended by the manufacturers. Competent *B. subtilis* cells were prepared as described by Ferrari E. and B. Miller (*Bacillus* expression: a Gram-Positive Model. In Gene Expression Systems: Using Nature for the Art of Expression. 1999. Academic Press, N.Y.).

PCR reactions were performed with Herculase enzyme (Stratagene) according to the manufacturer's instructions. The reaction contained 200 nM of each primer, 1 unit of Herculase and 200 μM of each dNTP. A PxE Thermal Cycler from Hybaid (Thermo) was used with the following cycle: denaturation at 94° C. for 3 min., followed by 30 cycle of denaturation at 94° C. for 30 s, annealing at 55° C. for 30 s and extension at 72° C. for 1 min/1 kbp to be amplified. The PCR reaction was then analyzed on 0.8% agarose e-gels from Invitrogen.

Genomic DNA was prepared using Eppendorf Phase Lock Gel tubes (Eppendorf) and their protocol.

D-alanine, D-cycloserine and β-chloro-D-alanine were obtained from Sigma.

Assay for Subtilisin

Assays for subtilisin were carried out as previously described (Estell, D. V., Graycar, T. P., Wells, J. A. (1985) J. Biol. Chem. 260, 6518-6521) in 0.1 M Tris buffer, pH 8.6 containing 1.6 mM N-succinyl-L-Ala-L-Ala-L-Pro-L-Phe-p-nitroanilide (Vega Biochemicals). The assay measures the increase in absorbance at 410 nm/min due to release of p-nitroaniline. Assays were performed under initial rate conditions. A protease unit is defined as the amount of protease enzyme that increases the absorbance at 410 nm by 1 absorbance unit (AU) per minute of the standard solution described above at 25 C in a cuvette with 1 cm path length.

Bacterial Strains

*Escherichia coli* MM294: endA thiA hsdR17 supE44

*Bacillus subtilis* strains BG2190 (alr-) and BG2189 (alr-CmR) were described by Ferrari and Yang (1985) (Isolation of an alanine racemase gene from *Bacillus subtilis* and its use for plasmid maintenance in *B. subtilis*. Biotechnology, 3, 1003-1007 [1985]).

*B. subtilis* strain BG3594: nprE aprE spoIIE degU32 oppA

*B. subtilis* strain BG3594comK: This is *B. subtilis* BG3594 containing a xylR-PxylA-comK construct as described in WO 02/14490, which allows this strain to be made supercompetent (i.e. greater than 1% of a cell population is transformable with chromosomal *Bacillus* DNA).

*B. subtilis* strain CP3490: This is *B. subtilis* strain BG3594comK in which alr is knocked down (same mutation as in BG2190).

*B. subtilis* strain CP35491: This strain is *B. subtilis* strain BG3594 in which alr is knocked down (same mutation as in BG2190).

*B. subtilis* MDT01-138: This strain is *B. subtilis* strain BG3594 with an amplifiable cassette of the following structure: aprE 5'-subtilisin FNA-Chloramphenicol-aprE 5'. It has been amplified to Cm25.

*B. subtilis* strain CP4010: This strain is *B. subtilis* strain BG3594 comK with an amplifiable cassette of the following structure: aprE 5'-subtilisin FNA-alr-aprE 5'. It has been amplified using β-chloro-D-alanine.

*B. subtilis* strain CP4020: This strain is *B. subtilis* strain BG3594 with an amplifiable cassette of the following structure: aprE 5'-subtilisin FNA-alr-aprE 5'. It has been amplified using β-chloro-D-alanine.

*B. subtilis* strain Hyper1: has an amplified cassette encoding subtilisin FNA and containing a chloramphenicol marker.

CP3591: This strain is BG3594 with one copy of subtilisin FNA behind the aprE promoter in the oppA locus (i.e., 1 copy of subtilisin total).

CP3592: This is CP3591 with one additional copy of subtilisin FNA behind the aprE promoter between the ybdL and ybdM genes (i.e., 2 copies of subtilisin total).

CP3593: This is CP3592 with one additional copy of subtilisin FNA behind the aprE promoter in the pps locus (i.e., 3 copies of subtilisin total).

CP3594: This is CP3593 with one additional copy of subtilisin FNA behind the aprE promoter in the nprE locus (i.e., 4 copies of subtilisin total).

Plasmids pDALsub1 has been described in Ferrari et al. 1985. This plasmid expresses alr. (Ferrari and Yang, *Biotechnology*, 3, 1003-1007 [1985]).

pBSFNACm (Seq ID NO:1): this plasmid is a pBluescript derivative (Alting-Mees, M. A. and Short, J. M. pBluescript II: gene mapping vectors. Nucleic Acids Res. 17 (22), 9494 (1989)), containing f1 (IG)—the intergenic region of phage f1; rep (pMB1)—the pMB1 replicon responsible for the replication of phagemid; bla (ApR)—gene, coding for beta-lactamase that confers resistance to ampicillin; lacZ-5'-terminal part of lacZ gene encoding the N-terminal fragment of beta-galactosidase; a polypeptide expression cassette comprising aprE 5' region, a gene coding for a subtilisin (FNA), a chloramphenicol resistance gene from pC194 with its promoter, a repeat of the aprE 5' region. This plasmid is used to integrate the expression cassette in the 5' aprE region.

pBSFNAalr (Seq ID NO:2): this plasmid is derivative of pBSFNACm described above. In this plasmid, *B. subtilis* alr gene with its own promoter replaces the chloramphenicol-resistance gene. This plasmid is used to integrate the expression cassette in the 5' aprE region.

Media

LB and LB agar (LA), as described in Ausubel, F. M. et al. (eds) "Current Protocols in Molecular Biology". John Wiley and Sons, 1995. LBG 1% is LB supplemented with 10 g/L glucose. LBSM is LB agar supplemented with 1.6% skimmed milk FNII medium used to study protease production is described in WO05052146A2. Alr-strains are propagated on LB agar+100 mg/L D-alanine When appropriate, chloramphenicol, ampicillin, cycloserine or β-chloro-D-alanine was added to the plate or the broth.

Quantitative PCR (qPCR)

qPCR to quantify the copy number of the gene encoding the polypeptide of interest to be produced (e.g. subtilisin) was done on an ABI Prism 7000 Sequence Detection System (Applied Biosystems, Foster City, Calif.). The TaqMan Gene Expression Master Mix kit was used as instructed by the manufacturer (Applied Biosystems, Foster City, Calif.).

Fermentations

Strains to be tested were grown in 5 ml of LBG 1% in a 10-ml tube, at 37 C and 250 rpm. At an $OD_{600}$ of ~1, 2.5 ml of culture was used to inoculate 25 ml of FNII medium in 250-ml Erlenmeyer shake flasks. The shake flasks were incubated at 37° C. and 250 rpm, and broth samples were taken regularly to measure subtilisin activity.

Example 1

Determination of the Sensitivity Threshold of *Bacillus subtilis* BG3594 and BG3594, pDALsub1 to β-chloro-D-alanine (CDA)

In a first phase, the concentration of β-chloro-D-alanine (CDA) necessary to inhibit growth of *B. subtilis* was determined by plating dilutions of LB-grown strain BG3594 on LB agar plates containing different concentrations of CDA. As shown in Table 1, while BG3594 can still grow at a concentration of 20 mg/L, growth is totally inhibited at a concentration of 50 mg/L. In a second phase, pDalsub1 was transformed into BG3594 to determine if overexpression of alr can restore growth on inhibitory concentrations of CDA. As shown in Table 1, the presence of the alr-expressing plasmid allows growth on all CDA concentrations tested. This result indicates that a strain containing a chromosomally-encoded expression cassette "polypeptide of interest-alr" can grow on CDA concentrations higher than 20 mg/L only if amplification occurs. Other alanine racemase inhibitors, such as cycloserine, could be used instead of CDA.

TABLE 1

Resistance of BG3594 and BG3594, pDALsub1 to increasing concentration of β-chloro-D-alanine in a LB agar plate.

| | CDA mg/L | | | |
|---|---|---|---|---|
| | 0 | 20 | 50 | 100 |
| BG3594 | +* | + | −** | − |
| BG3594, pDALsub1 | + | + | + | + |

*+: growth.;
**−: no growth

Example 2

Construction of Strains Containing a Chromosomally-Encoded Expression Cassette "Polypeptide of Interest-Marker" (Strains BG4010 (comK) and BG4020)

The plasmid pBSFNAalr (SEQ ID NO:2) was constructed from pBSFNACm (SEQ ID NO:1) as follows. The *B. subtilis* alr gene with its own promoter was PCR-amplified using chromosomal DNA as a template. Primers used were EcoRIDrdIalrF (having a DrdI site; gaagaattcg actaggttgt cttttcgtta gacatcgttt ccctttagc; SEQ ID NO:3) and SmaI-alrR (having a SmaI site; ggttcccggg ttaattgctt atatttacct gcaataaagg; SEQ ID NO:4). The PCR product was digested with DrdI/SmaI and religated with the bigger fragment of BsmI/StuI-th digested pBSFNACm. The ligation was transformed in *E. coli* strain MM294 and plated on carbenicillin 50 ppm. Four colonies from this transformation were inoculated in 5 ml LB+carbenicillin 50 ppm for plasmid purification. The resultant construct was called pBSFNAalr (SEQ ID NO:2).

pBSFNACm (SEQ ID NO: 1)

(SEQ ID NO: 1)

```
ctaaattgta agcgttaata ttttgttaaa attcgcgtta aattttttgtt aaatcagctc    60 atttttaac  caataggccg aaatcggcaa atcccttat  aaatcaaaag aatagaccga   120 gataggttg  agtgttgttc cagtttggaa caagagtcca ctattaaaga acgtggactc   180
caacgtcaaa gggcgaaaaa ccgtctatca gggcgatggc ccactacgtg aaccatcacc   240
ctaatcaagt tttttggggt cgaggtgccg taaagcacta aatcggaacc ctaaagggag   300
cccccgattt  agagcttgac ggggaaagcc ggcgaacgtg gcgagaaagg aagggaagaa   360
agcgaaagga gcggcgcta  gggcgctggc aagtgtagcg gtcacgctgc gcgtaaccac   420
cacacccgcc gcgcttaatg cgccgctaca gggcgcgtcc cattcgccat tcaggctgcg   480
caactgttgg gaagggcgat cggtgcgggc ctcttcgcta ttacgccagc tggcgaaagg   540
gggatgtgct gcaaggcgat taagttgggt aacgccaggg ttttcccagt cacgacgttg   600
taaaacgacg gccagtgagc gcgcgtaata cgactcacta tagggcgaat tggagctcca   660
ccgcggtggc ggccgctcta gaactagtgg atccccgggg ctgcaggaat tctccatttt   720
cttctgctat caaataaca  gactcgtgat tttccaaacg agctttcaaa aaagcctctg   780
ccccttgcaa atcggatgcc tgtctataaa attcccgata ttggttaaac agcggcgcaa   840
tggcggccgc atctgatgtc tttgcttggc gaatgttcat cttatttctt cctccctctc   900
aataattttt tcattctatc cctttctgt  aaagtttatt tttcagaata cttttatcat   960
catgctttga aaaaatatca cgataatatc cattgttctc acggaagcac acgcaggtca  1020
```

-continued

```
tttgaacgaa ttttttcgac aggaatttgc cgggactcag gagcatttaa cctaaaaaag 1080
catgacattt cagcataatg aacatttact catgtctatt ttcgttcttt tctgtatgaa 1140
aatagttatt tcgagtctct acggaaatag cgagagatga tatacctaaa tagagataaa 1200
atcatctcaa aaaaatgggt ctactaaaat attattccat ctattacaat aaattcacag 1260
aatagtcttt taagtaagtc tactctgaat ttttttaaaa ggagagggta aagagtgaga 1320
agcaaaaaat tgtggatcag tttgctgttt gctttagcgt taatctttac gatggcgttc 1380
ggcagcacat cctctgccca ggcggcaggg aaatcaaacg gggaaaagaa atatattgtc 1440
gggtttaaac agacaatgag cacgatgagc gccgctaaga agaaagatgt catttctgaa 1500
aaaggcggga aagtgcaaaa gcaattcaaa tatgtagacg cagcttcagc tacattaaac 1560
gaaaaagctg taaagaatt gaaaaaagac ccgagcgtcg cttacgttga agaagatcac 1620
gtagcacatg cgtacgcgca gtccgtgcct tacggcgtat cacaaattaa agcccctgct 1680
ctgcactctc aaggctacac tggatcaaat gttaaagtag cggttatcga cagcggtatc 1740
gattcttctc atcctgattt aaaggtagca ggcggagcca gcatggttcc ttctgaaaca 1800 aatccttttcc aagacaacaa ctctcacgga actcacgttg ccggcacagt gcggctctt 1860 aataactcaa tcggtgtatt aggcgttgcg ccaagcgcat cactttacgc tgtaaaagtt 1920
ctcggtgctg acggttccgg ccaatacagc tggatcatta acggaatcga gtgggcgatc 1980
gcaaacaata tggacgttat taacatgagc ctcggcggac cttctggttc tgctgcttta 2040
aaagcggcag ttgataaagc cgttgcatcc ggcgtcgtag tcgttgcggc agccggtaac 2100
gaaggcactt ccggcagctc aagcacagtg ggctaccctg gtaaataccc ttctgtcatt 2160
gcagtaggcg ctgttgacag cagcaaccaa agagcatctt tctcaagcgt aggacctgag 2220
cttgatgtca tggcacctgg cgtatctatc caaagcacgc ttcctggaaa caaatacggc 2280
gcgttgaacg gtacatcaat ggcatctccg cacgttgccg gagcggctgc tttgattctt 2340
tctaagcacc cgaactggac aaacactcaa gtccgcagca gtttagaaaa caccactaca 2400
aaacttggtg attcttttcta ctatggaaaa gggctgatca acgtacaggc ggcagctcag 2460
taaaacataa aaaccggcc ttggccccgc cggttttta ttatttttct tcctccgcat 2520
gttcaatccg ctccataatc gacggatggc tccctctgaa aattttaacg agaaacggcg 2580
ggttgacccg gctcagtccc gtaacggcca agtcctgaaa cgtctcaatc gccgcttccc 2640
ggtttccggt cagctcaatg ccgtaacggt cggcggcgtt ttcctgatac cgggagacgg 2700
cattcgtaat cggatcctct agagtcgatt tttacaagaa ttagctttat ataatttctg 2760 ttttttctaaa gttttatcag ctacaaaaga cagaaatgta ttgcaatctt caactaaatc 2820
catttgattc tctccaatat gacgtttaat aaatttctga atacttgat ttctttgttt 2880 tttctcagta tacttttcca tgttataaca cataaaaaca acttagtttt cacaaactat 2940
gacaataaaa aaagttgctt ttttcccctt ctatgtatgt tttttactag tcatttaaaa 3000
cgatacatta ataggtacga aaagcaact ttttttgcgc ttaaaaccag tcataccaat 3060
aacttaaggg taactagcct cgccggcaat agttaccctt attatcaaga taagaaagaa 3120
aaggattttt cgctacgctc aaatccttta aaaaacaca aaagaccaca ttttttaatg 3180
tggtctttat tcttcaacta agcaccccat tagttcaaca aacgaaaatt ggataaagtg 3240 ggatatttt aaaatatata tttatgttac agtaatattg acttttaaaa aaggattgat 3300
tctaatgaag aaagcagaca agtaagcctc ctaaattcac tttagataaa aatttaggag 3360
gcatatcaaa tgaactttaa taaaattgat ttagacaatt ggaagagaaa agagatattt 3420
aatcattatt tgaaccaaca aacgactttt agtataacca cagaaattga tattagtgtt 3480
```

-continued

```
ttataccgaa acataaaaca agaaggatat aaattttacc ctgcatttat tttcttagtg 3540
acaagggtga taaactcaaa tacagctttt agaactggtt acaatagcga cggagagtta 3600
ggttattggg ataagttaga gccactttat acaattttg atggtgtatc taaaacattc 3660
tctggtattt ggactcctgt aaagaatgac ttcaaagagt tttatgattt atacctttct 3720
gatgtagaga atataatgg ttcggggaaa ttgtttccca aaacacctat acctgaaaat 3780 gcttttctc tttctattat tccatggact tcatttactg ggtttaactt aaatatcaat 3840
aataatagta attaccttct acccattatt acagcaggaa aattcattaa taaaggtaat 3900
tcaatatatt taccgctatc tttacaggta catcattctg tttgtgatgg ttatcatgca 3960
ggattgttta tgaactctat tcaggaattg tcagataggc ctaatgactg gctttttataa 4020 tatgagataa tgccgactgt acttttaca gtcggttttc taatgtcact aacctgcccc 4080
gttagttgaa gaaggttttt atattacagc tccagatcca tatccttctt tttctgaacc 4140
gacttctcct ttttcgcttc tttattccaa ttgctttatt gacgttgagc ctcggaaccc 4200
ttaacaatcc caaaacttgt cgaatggtcg gcttaatagc tcacgctatg ccgacattcg 4260
tctgcaagtt tagttaaggg ttcttctcaa cgcacaataa attttctcgg cataaatgcg 4320
tggtctaatt tttatttta ataaccttga tagcaaaaaa tgccattcca atacaaaacc 4380
acatacctat aatcgaccgg aattaattct ccatttcttt ctgctatcaa ataacagac 4440 tcgtgatttt ccaaacgagc tttcaaaaaa gcctctgccc cttgcaaatc ggatgcctgt 4500
ctataaaatt cccgatattg gttaaacagc ggcgcaatgg cggccgcatc tgatgtcttt 4560
gcttggcgaa tgttcatctt atttcttcct ccctctcaat aattttttca ttctatccct 4620
tttctgtaaa gttatttttt cagaatactt ttatcatcat gctttgaaaa atatcacga 4680 taatatccat tgttctcacg gaagcacacg caggtcattt gaacgaattt tttcgacagg 4740
aatttgccgg gactcaggag catttaacct aaaaaagcat gacatttcag cataatgaac 4800
atttactcat gtctattttc gttcttttct gtatgaaaat agttatttcg agtctctacg 4860
gaaatagcga gagatgatat acctaaatag agataaaatc atctcaaaaa aatgggtcta 4920
ctaaaatatt attccatcta ttacaataaa ttcacagaat agtctttttaa gtaagtctac 4980 tctgaatttt tttatcaagc ttatcgatac cgtcgacctc gagggggggc ccggtaccca 5040
gcttttgttc cctttagtga gggttaattg cgcgcttggc gtaatcatgg tcatagctgt 5100
ttcctgtgtg aaattgttat ccgctcacaa ttccacacaa catacgagcc ggaagcataa 5160
agtgtaaagc ctggggtgcc taatgagtga gctaactcac attaattgcg ttgcgctcac 5220
tgcccgcttt ccagtcggga aacctgtcgt gccagctgca ttaatgaatc ggccaacgcg 5280
cggggagagg cggtttgcgt attgggcgct cttccgcttc ctcgctcact gactcgctgc 5340
gctcggtcgt tcggctgcgg cgagcggtat cagctcactc aaaggcggta atacggttat 5400
ccacagaatc aggggataac gcaggaaaga acatgtgagc aaaaggccag caaaaggcca 5460
ggaaccgtaa aaaggccgcg ttgctggcgt ttttccatag gctccgcccc cctgacgagc 5520
atcacaaaaa tcgacgctca gtcagaggt ggcgaaaccc gacaggacta taagatacc 5580 aggcgtttcc ccctggaagc tccctcgtgc gctctcctgt tccgaccctg ccgcttaccg 5640
gatacctgtc cgcctttctc ccttcgggaa gcgtggcgct ttctcatagc tcacgctgta 5700
ggtatctcag ttcggtgtag tcgttcgct ccaagctggg ctgtgtgcac gaaccccccg 5760
ttcagcccga ccgctgcgcc ttatccggta actatcgtct gagtccaac ccggtaagac 5820 acgacttatc gccactggca gcagccactg gtaacaggat tagcagagcg aggtatgtag 5880
```

-continued

```
gcggtgctac agagttcttg aagtggtggc ctaactacgg ctacactaga aggacagtat 5940
ttggtatctg cgctctgctg aagccagtta ccttcggaaa aagagttggt agctcttgat 6000
ccggcaaaca aaccaccgct ggtagcggtg gttttttgt ttgcaagcag cagattacgc 6060
gcagaaaaaa aggatctcaa gaagatcctt tgatcttttc tacggggtct gacgctcagt 6120
ggaacgaaaa ctcacgttaa gggattttgg tcatgagatt atcaaaaagg atcttcacct 6180
agatcctttt aaattaaaaa tgaagtttta atcaatcta aagtatatat gagtaaactt 6240
ggtctgacag ttaccaatgc ttaatcagtg aggcacctat ctcagcgatc tgtctatttc 6300
gttcatccat agttgcctga ctccccgtcg tgtagataac tacgatacgg gagggcttac 6360
catctggccc cagtgctgca atgataccgc gagacccacg ctcaccggct ccagatttat 6420
cagcaataaa ccagccagcc ggaagggccg agcgcagaag tggtcctgca actttatccg 6480
cctccatcca gtctattaat tgttgccggg aagctagagt aagtagttcg ccagttaata 6540
gtttgcgcaa cgttgttgcc attgctacag catcgtggt gtcacgctcg tcgtttggta 6600
tggcttcatt cagctccggt tcccaacgat caaggcgagt tacatgatcc cccatgttgt 6660
gcaaaaaagc ggttagctcc ttcggtcctc cgatcgttgt cagaagtaag ttggccgcag 6720
tgttatcact catggttatg gcagcactgc ataattctct tactgtcatg ccatccgtaa 6780
gatgcttttc tgtgactggt gagtactcaa ccaagtcatt ctgagaatag tgtatgcggc 6840
gaccgagttg ctcttgcccg gcgtcaatac gggataatac cgcgccacat agcagaactt 6900
taaaagtgct catcattgga aaacgttctt cggggcgaaa actctcaagg atcttaccgc 6960
tgttgagatc cagttcgatg taacccactc gtgcacccaa ctgatcttca gcatctttta 7020
cttttaccag cgtttctggg tgagcaaaaa caggaaggca aaatgccgca aaaagggaa 7080 taagggcgac acgaaaatgt tgaatactca tactcttcct ttttcaatat tattgaagca 7140
tttatcaggg ttattgtctc atgagcggat acatattga atgtatttag aaaaataaac 7200
aaataggggt tccgcgcaca tttccccgaa aagtgccac                        7239
``` pBSFNAa1r (SEQ ID NO: 2)

(SEQ ID NO: 2)

```
ctaaattgta agcgttaata ttttgttaaa attcgcgtta aatttttgtt aaatcagctc   60
attttttaac caataggccg aaatcggcaa atcccttat aaatcaaaag aatagaccga  120
gatagggttg agtgttgttc cagtttggaa caagagtcca ctattaaaga acgtggactc  180
caacgtcaaa gggcgaaaaa ccgtctatca gggcgatggc ccactacgtg aaccatcacc  240
ctaatcaagt tttttggggt cgaggtgccg taaagcacta atcggaacc ctaaagggag   300 cccccgattt agagcttgac ggggaaagcc ggcgaacgtg gcgagaaagg aagggaagaa  360
agcgaaagga gcgggcgcta gggcgctggc aagtgtagcg gtcacgctgc gcgtaaccac  420
cacacccgcc gcgcttaatg cgccgctaca gggcgcgtcc cattcgccat tcaggctgcg  480
caactgttgg gaagggcgat cggtgcgggc ctcttcgcta ttacgccagc tggcgaaagg  540
gggatgtgct gcaaggcgat taagttgggt aacgccaggg ttttcccagt cacgacgttg  600
taaaacgacg gccagtgagc gcgcgtaata cgactcacta gggcgaat tggagctcca  660 ccgcggtggc ggccgctcta gaactagtgg atccccggg ctgcaggaat tctccatttt  720
cttctgctat caaataaca gactcgtgat tttccaaacg agctttcaaa aaagcctctg  780
ccccttgcaa atcggatgcc tgtctataaa attcccgata tggttaaac agcggcgcaa  840 tggcggccgc atcgatgtc tttgcttggc gaatgttcat cttatttctt cctccctctc  900
aataattttt tcattctatc cctttctgt aagttatt tttcagaata cttttatcat  960
catgctttga aaaaatatca cgataatatc cattgttctc acggaagcac acgcaggtca 1020
```

```
tttgaacgaa ttttttcgac aggaatttgc cgggactcag gagcatttaa cctaaaaaag 1080
catgacattt cagcataatg aacatttact catgtctatt ttcgttcttt tctgtatgaa 1140
aatagttatt tcgagtctct acggaaatag cgagagatga tatacctaaa tagagataaa 1200
atcatctcaa aaaatgggt ctactaaaat attattccat ctattacaat aaattcacag 1260
aatagtcttt taagtaagtc tactctgaat tttttaaaa ggagagggta aagagtgaga 1320
agcaaaaaat tgtggatcag tttgctgttt gctttagcgt taatctttac gatggcgttc 1380
ggcagcacat cctctgccca ggcggcaggg aaatcaaacg gggaaaagaa atatattgtc 1440
gggtttaaac agacaatgag cacgatgagc gccgctaaga agaaagatgt catttctgaa 1500
aaaggcggga aagtgcaaaa gcaattcaaa tatgtagacg cagcttcagc tacattaaac 1560
gaaaaagctg taaagaatt gaaaaaagac ccgagcgtcg cttacgttga agaagatcac 1620
gtagcacatg cgtacgcgca gtccgtgcct tacggcgtat cacaaattaa agcccctgct 1680
ctgcactctc aaggctacac tggatcaaat gttaaagtag cggttatcga cagcggtatc 1740
gattcttctc atcctgattt aaaggtagca ggcggagcca gcatggttcc ttctgaaaca 1800
aatcctttcc aagacaacaa ctctcacgga actcacgttg ccggcacagt tgcggctctt 1860
aataactcaa tcggtgtatt aggcgttgcg ccaagcgcat cactttacgc tgtaaaagtt 1920
ctcggtgctg acggttccgg ccaatacagc tggatcatta acggaatcga gtgggcgatc 1980
gcaaacaata tggacgttat taacatgagc ctcggcggac cttctggttc tgctgcttta 2040
aaagcggcag ttgataaagc cgttgcatcc ggcgtcgtag tcgttgcggc agccggtaac 2100
gaaggcactt ccggcagctc aagcacagtg ggctaccctg gtaaataccc ttctgtcatt 2160
gcagtaggcg ctgttgacag cagcaaccaa agagcatctt tctcaagcgt aggacctgag 2220
cttgatgtca tggcacctgg cgtatctatc caaagcacgc ttcctggaaa caaatacggc 2280
gcgttgaacg gtacatcaat ggcatctccg cacgttgccg gagcggctgc tttgattctt 2340
tctaagcacc cgaactggac aaacactcaa gtccgcagca gtttagaaaa caccactaca 2400
aaacttggtg attcttttcta ctatggaaaa gggctgatca acgtacaggc ggcagctcag 2460
taaaacataa aaaaccggcc ttggccccgc cggtttttta ttatttttct tcctccgcat 2520
gttcaatccg ctccataatc gacggatggc tccctctgaa aattttaacg agaaacggcg 2580
ggttgacccg gctcagtccc gtaacggcca agtcctgaaa cgtctcaatc gccgcttccc 2640
ggtttccggt cagctcaatg ccgtaacggt cggcggcgtt ttcctgatac cgggagactt 2700
ttcgttagac atcgttttccc tttagccttt aattttagta tgatatgtaa atgatattga 2760
ataaaagcta ggaagtgtcg taatgagcac aaaacctttt tacagagata cgtgggcgga 2820
aattgacttg tccgcgataa aggaaaatgt cagcaatatg aaaaaacata tcggtgaaca 2880
tgtccacttg atggcagttg tgaaagcaaa cgcctacggg catggtgatg cagaaacagc 2940
aaaggctgct cttgacgcag gtgcttcatg cttggccgtg gccatttttgg atgaagcgat 3000
ttcactgcgc aaaaagggat tgaaggcgcc tatattggtg cttggcgcgg ttcccccgga 3060
gtatgtggca atcgctgctg agtatgacgt gaccttaaca ggttattctg ttgaatggct 3120
tcaggaggca gcccgccaca cgaaaaaagg ttctcttcat tttcatctga aggtcgatac 3180
ggggatgaac agacttggtg taaaaacaga ggaagaagtt cagaacgtga tggcaattct 3240
tgaccgcaac cctcgtttaa agtgcaaagg ggtatttacc cattttgcga cagcggatga 3300
aaaagaaaga ggctatttct taatgcagtt tgagcgcttt aaagagctga ttgctccgct 3360
gccgttaaag aatctaatgg tccactgcgc gaacagcgcc gctggactcc ggctgaaaaa 3420
```

```
aggcttttt  aatgcagtca  gattcggcat  cggcatgtat  ggccttcgcc  cgtctgctga 3480
catgtcggac  gagataccgt  ttcagctgcg  tccggcattt  accctgcatt  cgacactgtc 3540
acatgtcaaa  ctgatcagaa  aaggcgagag  cgtcagctac  ggagccgagt  acacagcgga 3600
aaaagacaca  tggatcggga  cggtgcctgt  aggctatgcg  gacggctggc  tccgaaaatt 3660
gaaagggacc  gacatccttg  tgaagggaaa  acgcctgaaa  attgccggcc  gaatttgcat 3720
ggaccaattt  atggtggagc  tggatcagga  atatccgccg  ggcacaaaag  tcacattaat 3780
aggccggcag  ggggatgaat  atatttccat  ggatgagatt  gcaggaaggc  tcgaaaccat 3840
taactatgag  gtggcctgta  caataagttc  ccgtgttccc  cgtatgtttt  tggaaaatgg 3900
gagtataatg  gaagtaagaa  atcctttatt  gcaggtaaat  ataagcaatt  aacctaatga 3960
ctggctttta  taatatgaga  taatgccgac  tgtacttttt  acagtcggtt  ttctaatgtc 4020
actaacctgc  cccgttagtt  gaagaaggtt  tttatattac  agctccagat  ccatatcctt 4080 cttttctga   accgacttct  ccttttcgc   ttctttattc  caattgcttt  attgacgttg 4140
agcctcggaa  cccttaacaa  tcccaaaact  tgtcgaatgg  tcggcttaat  agctcacgct 4200
atgccgacat  tcgtctgcaa  gtttagttaa  gggttcttct  caacgcacaa  taaattttct 4260
cggcataaat  gcgtggtcta  atttttattt  ttaataacct  tgatagcaaa  aaatgccatt 4320
ccaatacaaa  accacatacc  tataatcgac  ctgcaggaat  taattcctcc  attttcttct 4380
gctatcaaaa  taacagactc  gtgattttcc  aaacgagctt  caaaaaagc   ctctgcccct 4440 tgcaaatcgg  atgcctgtct  ataaaattcc  cgatattggc  ttaaacagcg  gcgcaatggc 4500
ggccgcatct  gatgtctttg  cttggcgaat  gttcatctta  tttcttcctc  cctctcaata 4560
attttttcat  tctatccctt  ttctgtaaag  tttatttttc  agaatacttt  tatcatcatg 4620
ctttgaaaaa  atatcacgat  aatatccatt  gttctcacgg  aagcacacgc  aggtcatttg 4680
aacgaatttt  ttcgacagga  atttgccggg  actcaggagc  atttaaccta  aaaaagcatg 4740
acatttcagc  ataatgaaca  tttactcatg  tctattttcg  ttcttttctg  tatgaaaata 4800
gttatttcga  gtctctacgg  aaatagcgag  agatgatata  cctaaataga  gataaaatca 4860
tctcaaaaaa  atgggtctac  taaaatatta  ttccatctat  tacaataaat  tcacagaata 4920 gtctttaag   taagtctact  ctgaattttt  ttatcaagct  tatcgatacc  gtcgacctcg 4980
agggggggcc  cggtacccag  cttttgttcc  ctttagtgag  ggttaattgc  gcgcttggcg 5040
taatcatggt  catagctgtt  tcctgtgtga  aattgttatc  cgctcacaat  tccacacaac 5100
atacgagccg  gaagcataaa  gtgtaaagcc  tggggtgcct  aatgagtgag  ctaactcaca 5160
ttaattgcgt  tgcgctcact  gcccgctttc  cagtcgggaa  acctgtcgtg  ccagctgcat 5220
taatgaatcg  gccaacgcgc  ggggagaggc  ggtttgcgta  ttgggcgctc  ttccgcttcc 5280
tcgctcactg  actcgctgcg  ctcggtcgtt  cggctgcggc  gagcggtatc  agctcactca 5340
aaggcggtaa  tacggttatc  cacagaatca  ggggataacg  caggaaagaa  catgtgagca 5400
aaaggccagc  aaaaggccag  gaaccgtaaa  aaggccgcgt  tgctggcgtt  tttccatagg 5460
ctccgccccc  ctgacgagca  tcacaaaaat  cgacgctcaa  gtcagaggtg  cgaaacccg  5520 acaggactat  aaagatacca  ggcgtttccc  cctggaagct  ccctcgtgcg  ctctcctgtt 5580
ccgaccctgc  cgcttaccgg  atacctgtcc  gcctttctcc  cttcgggaag  cgtggcgctt 5640
```

-continued
```
tctcatagct cacgctgtag gtatctcagt tcggtgtagg tcgttcgctc caagctgggc 5700
tgtgtgcacg aacccccgt tcagcccgac cgctgcgcct tatccggtaa ctatcgtctt 5760
gagtccaacc cggtaagaca cgacttatcg ccactggcag cagccactgg taacaggatt 5820
agcagagcga ggtatgtagg cggtgctaca gagttcttga agtggtggcc taactacggc 5880
tacactagaa ggacagtatt tggtatctgc gctctgctga agccagttac cttcggaaaa 5940
agagttggta gctcttgatc cggcaaacaa accaccgctg gtagcggtgg ttttttttgtt 6000 tgcaagcagc agattacgcg cagaaaaaaa ggatctcaag aagatccttt gatcttttct 6060
acggggtctg acgctcagtg gaacgaaaac tcacgttaag ggattttggt catgagatta 6120
tcaaaaagga tcttcaccta gatccttta aattaaaaat gaagttttaa atcaatctaa 6180
agtatatatg agtaaacttg gtctgacagt taccaatgct taatcagtga ggcacctatc 6240
tcagcgatct gtctatttcg ttcatccata gttgcctgac tccccgtcgt gtagataact 6300
acgatacggg agggcttacc atctggcccc agtgctgcaa tgataccgcg agacccacgc 6360
tcaccggctc cagatttatc agcaataaac cagccagccg gaagggccga gcgcagaagt 6420
ggtcctgcaa ctttatccgc ctccatccag tctattaatt gttgccggga agctagagta 6480
agtagttcgc cagttaatag tttgcgcaac gttgttgcca ttgctacagg catcgtggtg 6540
tcacgctcgt cgtttggtat ggcttcattc agctccggtt cccaacgatc aaggcgagtt 6600
acatgatccc ccatgttgtg caaaaaagcg gttagctcct tcggtcctcc gatcgttgtc 6660
agaagtaagt tggccgcagt gttatcactc atggttatgg cagcactgca taattctctt 6720
actgtcatgc catccgtaag atgcttttct gtgactggtg agtactcaac caagtcattc 6780
tgagaatagt gtatgcggcg accgagttgc tcttgcccgg cgtcaatacg ggataatacc 6840
gcgccacata gcagaacttt aaaagtgctc atcattggaa aacgttcttc ggggcgaaaa 6900
ctctcaagga tcttaccgct gttgagatcc agttcgatgt aacccactcg tgcacccaac 6960
tgatcttcag catcttttac tttcaccagc gtttctgggt gagcaaaaac aggaaggcaa 7020
aatgccgcaa aaaagggaat aagggcgaca cggaaatgtt gaatactcat actcttcctt 7080
tttcaatatt attgaagcat ttatcagggt tattgtctca tgagcggata catatttgaa 7140
tgtatttaga aaaataaaca aataggggtt ccgcgcacat ttccccgaaa agtgccac   7198
``` pBSFNAalr was digested with NotI/ScaI (buffer H), producing four fragments when run on gel. Sizes of the fragments were the following: 3660-2263-1105-174. The biggest piece, containing the cassette 5'-FNA-alr-5' was gel purified and ligated on itself. The ligation was done with the "rapid ligation" kit (Roche). The circular piece of DNA obtained was submitted to a rolling-circle reaction (Amersham kit) and transformed into competent cells of either CP3590 or CP3591 and plated on LA+1.6% skimmed milk, either BG3594 or BG3594comK and plated on LA+1.6% skimmed milk+50 ppm CDA. Strains with the correct construct would grow on those plates and show a halo due to skimmed milk clearing by the expressed protease.

The cassette can be passed in any strain by transformation with chromosomal DNA of the strains mentioned in the paragraph above and selection on CDA 50. Amplification of the cassette was done by streaking the strain on increasing amount of CDA (up to 200 ppm). Amplified strains have a bigger halo when plated on 1.6% skimmed milk, demonstrating that passing the strain on increasing amounts of CDA leads to amplification of the cassette.

Example 3

Determination of the Copy Number of SUBTILISIN Genes in Strain BG4020, Using qPCR Chromosomal DNA was extracted from strains CP3591, CP3592, CP3593, BG4020, BG4020 amplified and HyperI. DNA concentration was measured and samples were diluted to the same concentration for each sample. The same amount of DNA for each strain was then used in a qPCR reaction with primers annealing to the subtilisin gene (FNA-R2; ccagtgtagc cttgagag; SEQ ID NO:5 and FNA-F2; acaatgagca cgatgagc; SEQ ID NO:6).

Figure 3:
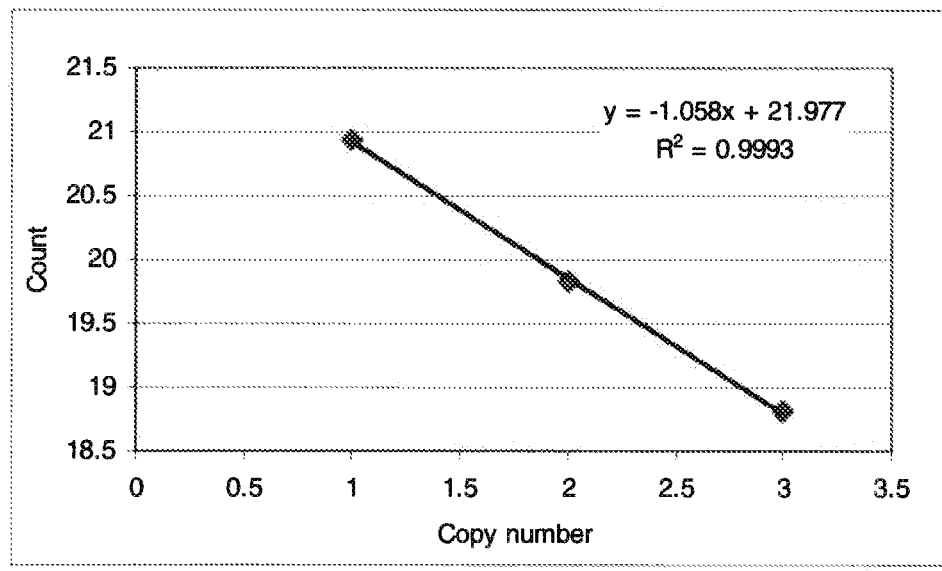
FIG. 3 shows a qPCR calibration curve.

Strains CP3591, CP3592 and CP3593, with 1, 2 and 3 copies of the gene, respectively, were used to build a calibration curve (FIG. 3). This calibration curve was used to determine subtilisin copy number in BG4020, BG4020 amplified and MDT01-138.

Table 2 provides the counts obtained from the qPCR reactions in BG4020, BG4020-amplified and HyperI strains. The corresponding subtilisin gene copy number was derived from the calibration curve given in FIG. 3. The results show that amplification with an alr marker (BG4020-amplified) is as efficient as amplification with the chloramphenicol marker (Hyper1); both BG4020-amplified and Hyper1 strains were determined to contain the same copy number i.e. 4). The non-integer number of copies in 4020 can result from a population of cells that do not homogenously contain the same number of copies of the amplified gene; and the value of 2.4 represents an average.

| Strain | Count | Copy number |
| --- | --- | --- |
| BG4020 | 19.473 | 2.4 |
| BG4020 amplified | 17.499 | 4.2 |
| Hyper1 | 17.665 | 4.1 |

Example 4

Production of a Polypeptide of Interest from Strains Amplified with a Cm or alr-Containing Cassette Strains to be tested were grown in 5 ml of LBG 1% in a 10-ml tube, at 37 C and 250 rpm. At an $OD_{600}$ of ~1, 2.5 ml of culture was used to inoculate 25 ml of FNII medium in 250-ml Erlenmeyer shake flasks. The shake flasks were incubated at 37° C. and 250 rpm, and broth samples were taken regularly to measure subtilisin activity. Four strains were tested in this way: BG3591 (contains one copy of the subtilisin gene, non-amplifiable), MDT01-138 (amplified using chloramphenicol), BG4020 (strain in which the cassette 5'-subtilisin-alr-5' has been introduced), BG4020-amplified (BG4020 strains that had been restreaked on increasing concentrations of CDA). MDT01-138 is a strain isogenic to Hyper1—it contains a chloraphenicol marker gene.

Figure 4:
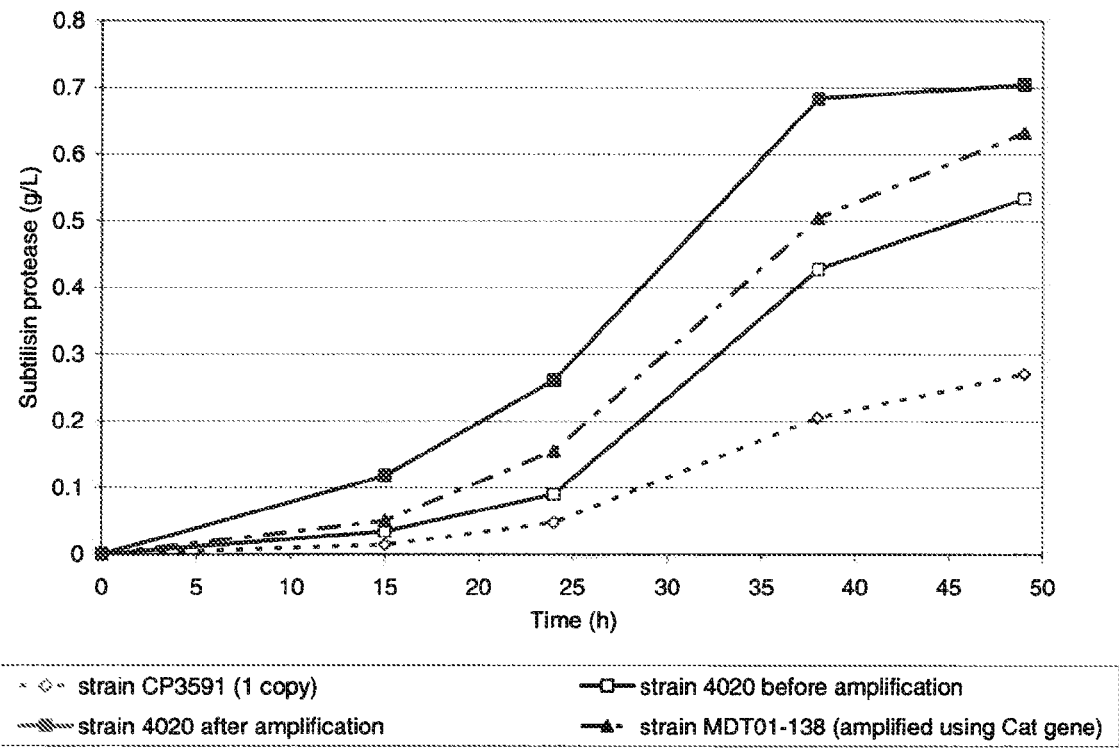
FIG. 4 is a graph showing subtilisin FNA expression levels from various host strains.

The amount of subtilisin protease produced in shake flasks by each of those strains is shown in FIG. 4. From this graph, the amplification of the subtilisin gene (BG4020-amplified) leads to higher protease production than a one-copy strain (BG3591) or a non-amplified strain (BG4020). In addition, the strain obtained by amplification using the alr marker (BG4020-amplified) produced more protease than the strain amplified using the chloramphenicol marker (MDT01-138).

These results show that the alr gene can be efficiently used as a non-antibiotic, non-exogenous marker for amplifying an expression cassette encoding a polypeptide of interest, and consequently producing high levels of the polypeptide of interest.

We claim:

1. A method of amplifying a genomic locus comprising:
   (a) contacting a population of bacterial host cells comprising a genomic locus of the structure:

$A_1$-P-M-$A_2$, wherein $A_1$ and $A_2$ are direct repeats, P comprises a coding sequence for a protein of interest, and M comprises a coding sequence for an essential enzyme, with an inhibitor of said essential enzyme, wherein the bacterial host cells do not comprise an inactivated endogenous gene encoding the essential enzyme M; and
   (b) selecting for cells that are resistant to said inhibitor; wherein cells that are resistant to said inhibitor have multiple copies of said amplification unit.

2. The method of claim 1, wherein said bacterial host cell is *Bacillus* sp. cell.

3. The method of claim 1, wherein said essential enzyme is a wild-type enzyme that is endogenous to said cell.

4. The method of claim 1, wherein P comprises an expression cassette.

5. The method of claim 1, wherein $A_1$ comprises a promoter that is operably linked to the coding sequence of P.

6. The method of claim 1, wherein said coding sequence for said essential enzyme is linked to a promoter that is endogenous to said coding sequence.

7. The method of claim 1, wherein said protein of interest is a substilisin.

8. The method of claim 1, wherein said essential enzyme is D-alanine racemase.

9. The method of claim 8, wherein said inhibitor is β-chloro-D-alanine.

10. A bacterial host cell comprising a genomic locus comprising multiple copies of an amplification unit of the structure:

$A_1$-P-M-$A_2$, wherein $A_1$ and $A_2$ are direct repeats, P comprises a coding sequence for a protein of interest, and M comprises a coding sequence of an essential enzyme, wherein the essential enzyme is an alanine racemase and wherein the bacterial host cell does not comprise an inactivated endogenous gene encoding the essential enzyme M.

11. The bacterial host cell of claim 10, wherein said protein of interest is a subtilisin, and said essential enzyme is alanine racemase.

12. The bacterial host cell of claim 10, wherein said amplification unit has a sequence set forth in SEQ ID NO: 7.

13. A bacterial cell culture comprising: growth medium; and a population of bacterial cells of claim 10.

14. A bacterial host cell comprising a genomic locus comprising multiple copies of an amplification unit of the structure:

$A_1$-P-M-$A_2$, wherein $A_1$ and $A_2$ are direct repeats, P comprises a first coding sequence for a protein of interest, and M comprises a second coding sequence for an essential enzyme, wherein said first coding sequence is operably linked to a promoter that is present in direct repeat $A_1$, wherein the essential enzyme is an alanine racemase and wherein the bacterial host cell does not comprise an inactivated endogenous gene encoding the essential enzyme M.

15. The bacterial host cell of claim 14, wherein said protein of interest is a subtilisin, and said essential enzyme is alanine racemase.

16. The bacterial host cell of claim 15, wherein said amplification unit has a sequence set forth in SEQ ID NO: 7.

* * * * *

SEQUENCE LISTING

<160> NUMBER OF SEQ ID NOS: 13

<210> SEQ ID NO 1
<211> LENGTH: 7239
<212> TYPE: DNA
<213> ORGANISM: Artificial
<220> FEATURE:
<223> OTHER INFORMATION: synthetic pBSFNACm plasmid

<400> SEQUENCE: 1

```
ctaaattgta agcgttaata ttttgttaaa attcgcgtta aattttttgtt aaatcagctc      60 atttttttaac caataggccg aaatcggcaa atcccttat aaatcaaaag aatagaccga     120
gatagggttg agtgttgttc cagtttggaa caagagtcca ctattaaaga acgtggactc     180
caacgtcaaa gggcgaaaaa ccgtctatca gggcgatggc ccactacgtg aaccatcacc     240
ctaatcaagt tttttggggt cgaggtgccg taaagcacta aatcggaacc ctaaaggag      300 cccccgattt agagcttgac ggggaaagcc ggcgaacgtg gcgagaaagg aagggaagaa     360
agcgaaagga gcgggcgcta gggcgctggc aagtgtagcg gtcacgctgc gcgtaaccac     420
cacacccgcc gcgcttaatg cgccgctaca gggcgcgtcc cattcgccat tcaggctgcg     480
caactgttgg gaagggcgat cggtgcgggc ctcttcgcta ttacgccagc tggcgaaagg     540
gggatgtgct gcaaggcgat taagttgggt aacgccaggg ttttcccagt cacgacgttg     600
taaaacgacg gccagtgagc gcgcgtaata cgactcacta tagggcgaat tggagctcca     660
ccgcggtggc ggccgctcta gaactagtgg atccccggg ctgcaggaat tctccatttt     720
cttctgctat caaaataaca gactcgtgat tttccaaacg agctttcaaa aaagcctctg     780
ccccttgcaa atcggatgcc tgtctataaa attcccgata ttggttaaac agcggcgcaa     840
tggcggccgc atctgatgtc tttgcttggc gaatgttcat cttattttctt cctccctctc     900 aataattttt tcattctatc ccttttctgt aaagtttatt tttcagaata cttttatcat     960
catgctttga aaaaatatca cgataatatc cattgttctc acggaagcac acgcaggtca    1020
tttgaacgaa ttttttcgac aggaatttgc cgggactcag gagcatttaa cctaaaaaag    1080
```

```
catgacattt cagcataatg aacatttact catgtctatt ttcgttcttt tctgtatgaa    1140
aatagttatt tcgagtctct acggaaatag cgagagatga tatacctaaa tagagataaa    1200
atcatctcaa aaaatgggt ctactaaaat attattccat ctattacaat aaattcacag     1260
aatagtcttt taagtaagtc tactctgaat ttttttaaaa ggagagggta aagagtgaga    1320
agcaaaaaat tgtggatcag tttgctgttt gctttagcgt taatctttac gatggcgttc    1380
ggcagcacat cctctgccca ggcggcaggg aaatcaaacg gggaaaagaa atatattgtc    1440
gggtttaaac agacaatgag cacgatgagc gccgctaaga agaaagatgt catttctgaa    1500
aaaggcggga aagtgcaaaa gcaattcaaa tatgtagacg cagcttcagc tacattaaac    1560
gaaaaagctg taaagaatt gaaaaaagac ccgagcgtcg cttacgttga agaagatcac     1620
gtagcacatg cgtacgcgca gtccgtgcct tacggcgtat cacaaattaa agcccctgct    1680
ctgcactctc aaggctacac tggatcaaat gttaaagtag cggttatcga cagcggtatc    1740
gattcttctc atcctgattt aaaggtagca ggcggagcca gcatggttcc ttctgaaaca    1800
aatcctttcc aagacaacaa ctctcacgga actcacgttg ccggcacagt tgcggctctt    1860
aataactcaa tcggtgtatt aggcgttgcg ccaagcgcat cactttacgc tgtaaaagtt    1920
ctcggtgctg acggttccgg ccaatacagc tggatcatta acggaatcga gtgggcgatc    1980
gcaaacaata tggacgttat taacatgagc ctcggcggac cttctggttc tgctgcttta    2040
aaagcggcag ttgataaagc cgttgcatcc ggcgtcgtag tcgttgcggc agccggtaac    2100
gaaggcactt ccggcagctc aagcacagtg gctaccctg gtaaatacc ttctgtcatt      2160 gcagtaggcg ctgttgacag cagcaaccaa agagcatctt tctcaagcgt aggacctgag    2220
cttgatgtca tggcacctgg cgtatctatc caaagcacgc ttcctggaaa caaatacggc    2280
gcgttgaacg gtacatcaat ggcatctccg cacgttgccg gagcggctgc tttgattctt    2340
tctaagcacc cgaactggac aaacactcaa gtccgcagca gtttagaaaa caccactaca    2400
aaacttggtg attcttttcta ctatggaaaa gggctgatca acgtacaggc ggcagctcag    2460
taaaacataa aaaaccggcc ttggccccgc cggttttta ttattttct tcctccgcat      2520 gttcaatccg ctccataatc gacgatggc tccctctgaa aattttaacg agaaacggcg    2580
ggttgacccg gctcagtccc gtaacggcca agtcctgaaa cgtctcaatc gccgcttccc    2640
ggtttccggt cagctcaatg ccgtaacggt cggcggcgtt ttcctgatac cgggagacgg    2700
cattcgtaat cggatcctct agagtcgatt tttacaagaa ttagctttat ataatttctg    2760 ttttttctaaa gttttatcag ctacaaaaga cagaaatgta ttgcaatctt caactaaatc    2820
catttgattc tctccaatat gacgtttaat aaatttctga atacttgat ttctttgttt     2880 tttctcagta tacttttcca tgttataaca cataaaaaca acttagtttt cacaaactat    2940
gacaataaaa aaagttgctt tttcccttt ctatgtatgt tttttactag tcatttaaaa     3000
cgatacatta ataggtacga aaagcaact tttttgcgc ttaaaaccag tcataccaat      3060
aacttaaggg taactagcct cgccggcaat agttaccctt attatcaaga taagaaagaa    3120
aaggattttt cgctacgctc aaatccttta aaaaacaca aaagaccaca ttttttaatg    3180
tggtctttat tcttcaacta aagcacccat tagttcaaca aacgaaaatt ggataaagtg    3240
ggatattttt aaaatatata tttatgttac agtaatattg acttttaaaa aaggattgat    3300
tctaatgaag aaagcagaca agtaagcctc ctaaattcac tttagataaa aatttaggag    3360
gcatatcaaa tgaactttaa taaaattgat ttagacaatt ggaagagaaa agagatattt    3420
aatcattatt tgaaccaaca aacgactttt agtataacca cagaaattga tattagtgtt    3480
```

```
ttataccgaa acataaaaca agaaggatat aaattttacc ctgcatttat tttcttagtg    3540
acaagggtga taaactcaaa tacagctttt agaactggtt acaatagcga cggagagtta    3600
ggttattggg ataagttaga gccactttat acaattttg atggtgtatc taaaacattc     3660
tctggtattt ggactcctgt aaagaatgac ttcaaagagt tttatgattt ataccttct     3720 gatgtagaga atataatgg ttcggggaaa ttgtttccca aaacacctat acctgaaaat     3780 gcttttctc tttctattat tccatggact tcatttactg ggtttaactt aaatatcaat     3840
aataatagta attaccttct acccattatt acagcaggaa aattcattaa taaaggtaat    3900
tcaatatatt taccgctatc tttacaggta catcattctg tttgtgatgg ttatcatgca    3960
ggattgttta tgaactctat tcaggaattg tcagataggc ctaatgactg ctttttataa    4020
tatgagataa tgccgactgt acttttaca gtcggttttc taatgtcact aacctgcccc     4080
gttagttgaa gaaggttttt atattacagc tccagatcca tatccttctt tttctgaacc    4140
gacttctcct ttttcgcttc tttattccaa ttgctttatt gacgttgagc ctcggaaccc    4200
ttaacaatcc caaaacttgt cgaatggtcg gcttaatagc tcacgctatg ccgacattcg    4260
tctgcaagtt tagttaaggg ttcttctcaa cgcacaataa attttctcgg cataaatgcg    4320
tggtctaatt tttattttta ataaccttga tagcaaaaaa tgccattcca atacaaaacc    4380 acataccat aatcgaccgg aattaattct ccatttctt ctgctatcaa ataacagac      4440 tcgtgatttt ccaaacgagc tttcaaaaaa gcctctgccc cttgcaaatc ggatgcctgt    4500
ctataaaatt cccgatattg gttaaacagc ggcgcaatgg cggccgcatc tgatgtcttt    4560
gcttggcgaa tgttcatctt atttcttcct ccctctcaat aatttttca ttctatccct     4620 tttctgtaaa gttatttttt cagaatactt ttatcatcat gctttgaaaa atatcacga    4680 taatatccat tgttctcacg gaagcacacg caggtcattt gaacgaattt tttcgacagg    4740
aatttgccgg gactcaggag catttaacct aaaaaagcat gacatttcag cataatgaac    4800
atttactcat gtctattttc gttcttttct gtatgaaaat agttatttcg agtctctacg    4860
gaaatagcga gagtgatat acctaaatag agataaaatc atctcaaaaa atgggtcta    4920 ctaaaatatt attccatcta ttacaataaa ttcacagaat agtctttaa gtaagtctac     4980 tctgaatttt tttatcaagc ttatcgatac cgtcgacctc gagggggggc ccggtaccca    5040
gcttttgttc cctttagtga gggttaattg cgcgcttggc gtaatcatgg tcatagctgt    5100
ttcctgtgtg aaattgttat ccgctcacaa ttccacacaa catacgagcc ggaagcataa    5160
agtgtaaagc ctggggtgcc taatgagtga gctaactcac attaattgcg ttgcgctcac    5220
tgcccgcttt ccagtcggga aacctgtcgt gccagctgca ttaatgaatc ggccaacgcg    5280
cggggagagg cggtttgcgt attgggcgct cttccgcttc ctcgctcact gactcgctgc    5340
gctcggtcgt tcggctgcgg cgagcggtat cagctcactc aaaggcggta atacggttat    5400
ccacagaatc aggggataac gcaggaaaga acatgtgagc aaaaggccag caaaaggcca    5460
ggaaccgtaa aaaggccgcg ttgctggcgt ttttccatag gctccgcccc cctgacgagc    5520
atcacaaaaa tcgacgctca gtcagaggt ggcgaaaccc gacaggacta taaagatacc     5580
aggcgtttcc ccctggaagc tccctcgtgc gctctcctgt tccgaccctg ccgcttaccg    5640
gatacctgtc cgcctttctc ccttcgggaa gcgtggcgct ttctcatagc tcacgctgta    5700
ggtatctcag ttcggtgtag gtcgttcgct ccaagctggg ctgtgtgcac gaaccccccg    5760
ttcagcccga ccgctgcgcc ttatccggta actatcgtct tgagtccaac ccggtaagac    5820
```

| | |
|---|---|
| acgacttatc gccactggca gcagccactg gtaacaggat tagcagagcg aggtatgtag | 5880 |
| gcggtgctac agagttcttg aagtggtggc ctaactacgg ctacactaga aggacagtat | 5940 |
| ttggtatctg cgctctgctg aagccagtta ccttcggaaa aagagttggt agctcttgat | 6000 |
| ccggcaaaca aaccaccgct ggtagcggtg gttttttgt ttgcaagcag cagattacgc | 6060 |
| gcagaaaaaa aggatctcaa gaagatcctt tgatctttc tacggggtct gacgctcagt | 6120 |
| ggaacgaaaa ctcacgttaa gggattttgg tcatgagatt atcaaaaagg atcttcacct | 6180 |
| agatcctttt aaattaaaaa tgaagtttta aatcaatcta agtatatat gagtaaactt | 6240 |
| ggtctgacag ttaccaatgc ttaatcagtg aggcacctat ctcagcgatc tgtctatttc | 6300 |
| gttcatccat agttgcctga ctccccgtcg tgtagataac tacgatacgg gagggcttac | 6360 |
| catctggccc cagtgctgca atgataccgc gagacccacg ctcaccggct ccagatttat | 6420 |
| cagcaataaa ccagccagcc ggaagggccg agcgcagaag tggtcctgca actttatccg | 6480 |
| cctccatcca gtctattaat tgttgccggg aagctagagt aagtagttcg ccagttaata | 6540 |
| gtttgcgcaa cgttgttgcc attgctacag gcatcgtggt gtcacgctcg tcgtttggta | 6600 |
| tggcttcatt cagctccggt tcccaacgat caaggcgagt tacatgatcc cccatgttgt | 6660 |
| gcaaaaaagc ggttagctcc ttcggtcctc cgatcgttgt cagaagtaag ttggccgcag | 6720 |
| tgttatcact catggttatg gcagcactgc ataattctct tactgtcatg ccatccgtaa | 6780 |
| gatgcttttc tgtgactggt gagtactcaa ccaagtcatt ctgagaatag tgtatgcggc | 6840 |
| gaccgagttg ctcttgcccg gcgtcaatac gggataatac cgcgccacat agcagaactt | 6900 |
| taaaagtgct catcattgga aaacgttctt cggggcgaaa actctcaagg atcttaccgc | 6960 |
| tgttgagatc cagttcgatg taacccactc gtgcacccaa ctgatcttca gcatctttta | 7020 |
| ctttcaccag cgtttctggg tgagcaaaaa caggaaggca aaatgccgca aaaaagggaa | 7080 |
| taagggcgac acggaaatgt tgaatactca tactcttcct ttttcaatat tattgaagca | 7140 |
| tttatcaggg ttattgtctc atgagcggat acatatttga atgtatttag aaaaataaac | 7200 |
| aaatagggt tccgcgcaca tttccccgaa aagtgccac | 7239 |

<210> SEQ ID NO 2
<211> LENGTH: 7198
<212> TYPE: DNA
<213> ORGANISM: Artificial
<220> FEATURE:
<223> OTHER INFORMATION: synthetic pBSFNalr plasmid

<400> SEQUENCE: 2

| | |
|---|---|
| ctaaattgta agcgttaata ttttgttaaa attcgcgtta aattttttgtt aaatcagctc | 60 |
| attttttaac caataggccg aaatcggcaa aatcccttat aaatcaaaag aatagaccga | 120 |
| gatagggttg agtgttgttc cagtttggaa caagagtcca ctattaaaga acgtggactc | 180 |
| caacgtcaaa gggcgaaaaa ccgtctatca gggcgatggc ccactacgtg aaccatcacc | 240 |
| ctaatcaagt tttttggggt cgaggtgccg taaagcacta aatcggaacc ctaaagggag | 300 |
| cccccgattt agagcttgac ggggaaagcc ggcgaacgtg gcgagaaagg aagggaagaa | 360 |
| agcgaaagga gcgggcgcta gggcgctggc aagtgtagcg gtcacgctgc gcgtaaccac | 420 |
| cacacccgcc gcgcttaatg cgccgctaca gggcgcgtcc cattcgccat tcaggctgcg | 480 |
| caactgttgg gaaggcgat cggtgcgggc ctcttcgcta ttacgccagc tggcgaaagg | 540 |
| gggatgtgct gcaaggcgat taagttgggt aacgccaggg ttttcccagt cacgacgttg | 600 |
| taaaacgacg gccagtgagc gcgcgtaata cgactcacta tagggcgaat tggagctcca | 660 |

```
ccgcggtggc ggccgctcta gaactagtgg atccccgggg ctgcaggaat tctccatttt    720
cttctgctat caaaataaca gactcgtgat tttccaaacg agctttcaaa aaagcctctg    780
ccccttgcaa atcggatgcc tgtctataaa attcccgata ttggttaaac agcggcgcaa    840
tggcggccgc atctgatgtc tttgcttggc gaatgttcat cttatttctt cctccctctc    900
aataattttt tcattctatc cctttctgt aaagtttatt tttcagaata cttttatcat     960
catgctttga aaaatatca cgataatatc cattgttctc acggaagcac acgcaggtca   1020
tttgaacgaa ttttttcgac aggaatttgc cgggactcag gagcatttaa cctaaaaaag   1080
catgacattt cagcataatg aacatttact catgtctatt ttcgttcttt tctgtatgaa   1140
aatagttatt tcgagtctct acggaaatag cgagagatga tatacctaaa tagagataaa   1200
atcatctcaa aaaatgggt ctactaaaat attattccat ctattacaat aaattcacag    1260
aatagtcttt taagtaagtc tactctgaat tttttaaaa ggagagggta aagagtgaga    1320
agcaaaaaat tgtggatcag tttgctgttt gctttagcgt taatctttac gatggcgttc   1380
ggcagcacat cctctgccca ggcggcaggg aaatcaaacg gggaaaagaa atatattgtc   1440
gggtttaaac agacaatgag cacgatgagc gccgctaaga agaaagatgt catttctgaa   1500
aaaggcggga agtgcaaaa gcaattcaaa tatgtagacg cagcttcagc tacattaaac    1560
gaaaaagctg taaagaatt gaaaaaagac ccgagcgtcg cttacgttga agaagatcac    1620
gtagcacatg cgtacgcgca gtccgtgcct tacggcgtat cacaaattaa agccctgct    1680 ctgcactctc aaggctacac tggatcaaat gttaaagtag cggttatcga cagcggtatc   1740
gattcttctc atcctgattt aaaggtagca ggcggagcca gcatggttcc ttctgaaaca   1800
aatcctttcc aagacaacaa ctctcacgga actcacgttg ccggcacagt tgcggctctt   1860
aataactcaa tcggtgtatt aggcgttgcg ccaagcgcat cactttacgc tgtaaaagtt   1920
ctcggtgctg acggttccgg ccaatacagc tggatcatta acggaatcga gtgggcgatc   1980
gcaaacaata tggacgttat taacatgagc ctcggcggac cttctggttc tgctgcttta   2040
aaagcggcag ttgataaagc cgttgcatcc ggcgtcgtag tcgttgcggc agccggtaac   2100
gaaggcactt ccggcagctc aagcacagtg gctaccctg gtaaataccc ttctgtcatt    2160
gcagtaggcg ctgttgacag cagcaaccaa agagcatctt tctcaagcgt aggacctgag   2220
cttgatgtca tggcacctgg cgtatctatc caaagcacgc ttcctggaaa caaatacggc   2280
gcgttgaacg gtacatcaat ggcatctccg cacgttgccg gagcggctgc tttgattctt   2340
tctaagcacc cgaactggac aaacactcaa gtccgcagca gtttagaaaa caccactaca   2400
aaacttggtg attctttcta ctatggaaaa gggctgatca acgtacaggc ggcagctcag   2460
taaaacataa aaaccggcc ttggccccgc cggttttta ttattttct cctccgcat       2520 gttcaatccg ctccataatc gacggatggc tccctctgaa aattttaacg agaaacggcg   2580
ggttgacccg gctcagtccc gtaacggcca agtcctgaaa cgtctcaatc gccgcttccc   2640
ggtttccggt cagctcaatg ccgtaacggt cggcggcgtt ttcctgatac cgggagactt   2700
ttcgttagac atcgtttccc tttagccttt aattttagta tgatatgtaa atgatattga   2760
ataaaagcta ggaagtgtcg taatgagcac aaaacctttt tacagagata cgtgggcgga   2820
aattgacttg tccgcgataa aggaaaatgt cagcaatatg aaaaaacata tcggtgaaca   2880
tgtccacttg atggcagttg tgaaagcaaa cgcctacggg catggtgatg cagaaacagc   2940
aaaggctgct cttgacgcag gtgcttcatg cttggccgtg gccatttggg atgaagcgat   3000
```

```
ttcactgcgc aaaaagggat tgaaggcgcc tatattggtg cttggcgcgg ttcccccgga    3060
gtatgtggca atcgctgctg agtatgacgt gaccttaaca ggttattctg ttgaatggct    3120
tcaggaggca gcccgccaca cgaaaaaagg ttctcttcat tttcatctga aggtcgatac    3180
ggggatgaac agacttggtg taaaaacaga ggaagaagtt cagaacgtga tggcaattct    3240
tgaccgcaac cctcgtttaa agtgcaaagg ggtatttacc cattttgcga cagcggatga    3300
aaaagaaaga ggctatttct taatgcagtt tgagcgcttt aaagagctga ttgctccgct    3360
gccgttaaag aatctaatgg tccactgcgc gaacagcgcc gctggactcc ggctgaaaaa    3420 aggcttttt  aatgcagtca gattcggcat cggcatgtat ggccttcgcc cgtctgctga    3480
catgtcggac gagataccgt ttcagctgcg tccggcattt accctgcatt cgacactgtc    3540
acatgtcaaa ctgatcagaa aaggcgagag cgtcagctac ggagccgagt acacagcgga    3600
aaaagacaca tggatcggga cggtgcctgt aggctatgcg gacggctggc tccgaaaatt    3660
gaaagggacc gacatccttg tgaagggaaa acgcctgaaa attgccggcc gaatttgcat    3720
ggaccaattt atggtggagc tggatcagga atatccgccg ggcacaaaag tcacattaat    3780
aggccggcag ggggatgaat atatttccat ggatgagatt gcaggaaggc tcgaaaccat    3840
taactatgag gtggcctgta caataagttc ccgtgttccc cgtatgtttt tggaaaatgg    3900
gagtataatg gaagtaagaa atcctttatt gcaggtaaat ataagcaatt aacctaatga    3960
ctggctttta taatatgaga taatgccgac tgtactttt  acagtcggtt ttctaatgtc    4020
actaacctgc cccgttagtt gaagaaggtt tttatattac agctccagat ccatatcctt    4080
ctttttctga accgacttct ccttttcgc  ttctttattc caattgcttt attgacgttg    4140
agcctcggaa cccttaacaa tcccaaaact tgtcgaatgg tcggcttaat agctcacgct    4200
atgccgacat tcgtctgcaa gtttagttaa gggttcttct caacgcacaa taaattttct    4260
cggcataaat gcgtggtcta atttttattt ttaataacct tgatagcaaa aaatgccatt    4320
ccaatacaaa accacatacc tataatcgac ctgcaggaat taattcctcc attttcttct    4380
gctatcaaaa taacagactc gtgattttcc aaacgagctt caaaaaagc  ctctgcccct    4440 tgcaaatcgg atgcctgtct ataaaattcc cgatattggc ttaaacagcg gcgcaatggc    4500
ggccgcatct gatgtctttg cttggcgaat gttcatctta tttcttcctc cctctcaata    4560
attttttcat tctatccctt ttctgtaaag tttattttc  agaatacttt tatcatcatg    4620
ctttgaaaaa atatcacgat aatatccatt gttctcacgg aagcacacgc aggtcatttg    4680 aacgaattt  ttcgacagga atttgccggg actcaggagc atttaaccta aaaaagcatg    4740
acatttcagc ataatgaaca tttactcatg tctattttcg ttcttttctg tatgaaaata    4800 gttattcga  gtctctacgg aaatagcgag agatgatata cctaaataga gataaaatca    4860
tctcaaaaaa atgggtctac taaaatatta ttccatctat tacaataaat tcacagaata    4920 gtctttaag  taagtctact ctgaattttt ttatcaagct tatcgatacc gtcgacctcg    4980 aggggggcc  cggtacccag cttttgttcc ctttagtgag ggttaattgc gcgcttggcg    5040
taatcatggt catagctgtt tcctgtgtga aattgttatc cgctcacaat tccacacaac    5100
atacgagccg gaagcataaa gtgtaaagcc tggggtgcct aatgagtgag ctaactcaca    5160
ttaattgcgt tgcgctcact gcccgctttc cagtcgggaa acctgtcgtg ccagctgcat    5220
taatgaatcg gccaacgcgc ggggagaggc ggtttgcgta ttgggcgctc ttccgcttcc    5280
tcgctcactg actcgctgcg ctcggtcgtt cggctgcggc gagcggtatc agctcactca    5340
aaggcggtaa tacggttatc cacagaatca ggggataacg caggaaagaa catgtgagca    5400
```

```
aaaggccagc aaaaggccag gaaccgtaaa aaggccgcgt tgctggcgtt tttccatagg    5460
ctccgccccc ctgacgagca tcacaaaaat cgacgctcaa gtcagaggtg gcgaaacccg    5520
acaggactat aaagatacca ggcgtttccc cctggaagct ccctcgtgcg ctctcctgtt    5580
ccgaccctgc cgcttaccgg atacctgtcc gcctttctcc cttcgggaag cgtggcgctt    5640
tctcatagct cacgctgtag gtatctcagt tcggtgtagg tcgttcgctc caagctgggc    5700
tgtgtgcacg aaccccccgt tcagcccgac cgctgcgcct tatccggtaa ctatcgtctt    5760
gagtccaacc cggtaagaca cgacttatcg ccactggcag cagccactgg taacaggatt    5820
agcagagcga ggtatgtagg cggtgctaca gagttcttga agtggtggcc taactacggc    5880
tacactagaa ggacagtatt tggtatctgc gctctgctga agccagttac cttcggaaaa    5940
agagttggta gctcttgatc cggcaaacaa accaccgctg gtagcggtgg ttttttttgtt    6000
tgcaagcagc agattacgcg cagaaaaaaa ggatctcaag aagatccttt gatcttttct    6060
acggggtctg acgctcagtg gaacgaaaac tcacgttaag gattttggt catgagatta    6120
tcaaaaagga tcttcaccta gatccttta aattaaaaat gaagttttaa atcaatctaa    6180
agtatatatg agtaaacttg gtctgacagt taccaatgct taatcagtga ggcacctatc    6240
tcagcgatct gtctatttcg ttcatccata gttgcctgac tccccgtcgt gtagataact    6300
acgatacggg agggcttacc atctggcccc agtgctgcaa tgataccgcg agacccacgc    6360
tcaccggctc cagatttatc agcaataaac cagccagccg aagggccga gcgcagaagt    6420
ggtcctgcaa ctttatccgc ctccatccag tctattaatt gttgccggga agctagagta    6480
agtagttcgc cagttaatag tttgcgcaac gttgttgcca ttgctacagg catcgtggtg    6540
tcacgctcgt cgtttggtat ggcttcattc agctccggtt cccaacgatc aaggcgagtt    6600
acatgatccc ccatgttgtg caaaaaagcg gttagctcct tcggtcctcc gatcgttgtc    6660
agaagtaagt tggccgcagt gttatcactc atggttatgg cagcactgca taattctctt    6720
actgtcatgc catccgtaag atgcttttct gtgactggtg agtactcaac caagtcattc    6780
tgagaatagt gtatgcggcg accgagttgc tcttgcccgg cgtcaatacg ggataatacc    6840
gcgccacata gcagaacttt aaaagtgctc atcattggaa aacgttcttc ggggcgaaaa    6900
ctctcaagga tcttaccgct gttgagatcc agttcgatgt aacccactcg tgcacccaac    6960
tgatcttcag catcttttac tttcaccagc gtttctgggt gagcaaaaac aggaaggcaa    7020
aatgccgcaa aaagggaat aagggcgaca cggaaatgtt gaatactcat actcttcctt    7080
tttcaatatt attgaagcat ttatcagggt tattgtctca tgagcggata catatttgaa    7140
tgtatttaga aaaataaaca aatagggtt ccgcgcacat ttccccgaaa agtgccac     7198
```

<210> SEQ ID NO 3
<211> LENGTH: 49
<212> TYPE: DNA
<213> ORGANISM: Artificial
<220> FEATURE:
<223> OTHER INFORMATION: synthetic primer

<400> SEQUENCE: 3
gaagaattcg actaggttgt cttttcgtta gacatcgttt cccttagc                 49

<210> SEQ ID NO 4
<211> LENGTH: 40
<212> TYPE: DNA
<213> ORGANISM: Artificial
<220> FEATURE:

<223> OTHER INFORMATION: synthetic primer

<400> SEQUENCE: 4
ggttcccggg ttaattgctt atatttacct gcaataaagg                               40

<210> SEQ ID NO 5
<211> LENGTH: 18
<212> TYPE: DNA
<213> ORGANISM: Artificial
<220> FEATURE:
<223> OTHER INFORMATION: synthetic primer

<400> SEQUENCE: 5
ccagtgtagc cttgagag                                                       18

<210> SEQ ID NO 6
<211> LENGTH: 18
<212> TYPE: DNA
<213> ORGANISM: Artificial
<220> FEATURE:
<223> OTHER INFORMATION: synthetic primer

<400> SEQUENCE: 6
acaatgagca cgatgagc                                                       18

<210> SEQ ID NO 7
<211> LENGTH: 4241
<212> TYPE: DNA
<213> ORGANISM: Artificial
<220> FEATURE:
<223> OTHER INFORMATION: synthetic amplification unit

<400> SEQUENCE: 7
tccattttct tctgctatca aaataacaga ctcgtgattt ccaaacgag ctttcaaaaa            60
agcctctgcc ccttgcaaat cggatgcctg tctataaaat tcccgatatt ggttaaacag          120
cggcgcaatg gcggccgcat ctgatgtctt tgcttggcga atgttcatct tatttcttcc          180
tccctctcaa taattttttc attctatccc ttttctgtaa agtttatttt tcagaatact          240
tttatcatca tgcttttgaaa aaatatcacg ataatatcca ttgttctcac ggaagcacac         300
gcaggtcatt tgaacgaatt ttttcgacag gaatttgccg ggactcagga gcatttaacc          360
taaaaaagca tgacatttca gcataatgaa catttactca tgtctatttt cgttcttttc          420
tgtatgaaaa tagttatttc gagtctctac ggaaatagcg agagatgata tacctaaata          480
gagataaaat catctcaaaa aaatgggtct actaaaatat tattccattt attacaataa          540
attcacagaa tagtctttta agtaagtcta ctctgaattt ttttaaaagg agagggtaaa          600
gagtgagaag caaaaaattg tggatcagtt tgctgttttgc tttagcgtta atctttacga         660
tggcgttcgg cagcacatcc tctgcccagg cggcagggaa atcaaacggg gaaaagaaat          720
atattgtcgg gtttaaacag acaatgagca cgatgagcgc cgctaagaag aaagatgtca          780
tttctgaaaa aggcgggaaa gtgcaaaagc aattcaaata tgtagacgca gcttcagcta          840
cattaaacga aaaagctgta aagaattga aaaagaccc gagcgtcgct tacgttgaag             900
aagatcacgt agcacatgcg tacgcgcagt ccgtgcctta cggcgtatca caaattaaag          960
cccctgctct gcactctcaa ggctacactg atcaaatgt taaagtagcg gttatcgaca          1020
gcggtatcga ttcttctcat cctgatttaa aggtagcagg cggagccagc atggttcctt         1080
ctgaaacaaa tccttttcca gacaacaact ctcacggaac tcacgttgcc ggcacagttg          1140
cggctcttaa taactcaatc ggtgtattag gcgttgcgcc aagcgcatca ctttacgctg         1200

```
taaaagttct cggtgctgac ggttccggcc aatacagctg gatcattaac ggaatcgagt   1260
gggcgatcgc aaacaatatg gacgttatta acatgagcct cggcggacct tctggttctg   1320
ctgctttaaa agcggcagtt gataaagccg ttgcatccgg cgtcgtagtc gttgcggcag   1380
ccggtaacga aggcacttcc ggcagctcaa gcacagtggg ctaccctggt aaatacccctt  1440
ctgtcattgc agtaggcgct gttgacagca gcaaccaaag agcatctttc tcaagcgtag   1500
gacctgagct tgatgtcatg gcacctggcg tatctatcca aagcacgctt cctgaaaaca   1560
aatacggcgc gttgaacggt acatcaatgg catctccgca cgttgccgga gcggctgctt   1620
tgattctttc taagcacccg aactggacaa acactcaagt ccgcagcagt ttagaaaaca   1680
ccactacaaa acttggtgat tctttctact atggaaaagg gctgatcaac gtacaggcgg   1740
cagctcagta aaacataaaa aaccggcctt ggccccgccg gttttttatt atttttcttc   1800
ctccgcatgt tcaatccgct ccataatcga cggatggctc cctctgaaaa ttttaacgag   1860
aaacggcggt tgacccggc tcagtcccgt aacggccaag tcctgaaacg tctcaatcgc    1920
cgcttcccgg tttccggtca gctcaatgcc gtaacggtcg cggcgttttt cctgataccg   1980
ggagactttt cgttagacat cgtttccctt tagcctttaa ttttagtatg atatgtaaat   2040
gatattgaat aaaagctagg aagtgtcgta atgagcacaa aacctttta cagagatacg    2100
tgggcggaaa ttgacttgtc cgcgataaag gaaaatgtca gcaatatgaa aaacatatc    2160
ggtgaacatg tccacttgat ggcagttgtg aaagcaaacg cctacgggca tggtgatgca   2220
gaaacagcaa aggctgctct tgacgcaggt gcttcatgct tggccgtggc catttttggat  2280
gaagcgattt cactgcgcaa aaagggattg aaggcgccta tattggtgct tggcgcggtt   2340
cccccggagt atgtggcaat cgctgctgag tatgacgtga ccttaacagg ttattctgtt   2400
gaatggcttc aggaggcagc ccgccacacg aaaaaaggtt ctcttcattt tcatctgaag   2460
gtcgatacgg ggatgaacag acttggtgta aaaacagagg aagaagttca gaacgtgatg   2520
gcaattcttg accgcaaccc tcgtttaaag tgcaaggggg tatttacccca ttttgcgaca   2580
gcggatgaaa aagaaagagg ctatttctta atgcagtttg agcgctttaa agagctgatt   2640
gctccgctgc cgttaaagaa tctaatggtc cactgcgcga cagcgccgc tggactccgg    2700
ctgaaaaaag gcttttttaa tgcagtcaga ttcggcatcg gcatgtatgg ccttcgcccg   2760
tctgctgaca tgtcggacga gataccgttt cagctgcgtc cggcatttac cctgcattcg   2820
acactgtcac atgtcaaact gatcagaaaa ggcgagagcg tcagctacgg agccgagtac   2880
acagcggaaa aagacacatg gatcgggacg gtgcctgtag gctatgcgga cggctggctc   2940
cgaaaattga agggaccga catccttgtg aagggaaaac gcctgaaaat tgccggccga    3000
atttgcatgg accaatttat ggtggagctg atcaggaat atccgccggg cacaaaagtc    3060
acattaatag gccggcaggg ggatgaatat atttccatgg atgagattgc aggaaggctc   3120
gaaaccatta actatgaggt ggcctgtaca ataagttccc gtgttccccg tatgtttttg   3180
gaaaatggga gtataatgga agtaagaaat cctttattgc aggtaaatat aagcaattaa   3240
cctaatgact ggcttttata atatgagata atgccgactg tacttttac agtcggtttt    3300
ctaatgtcac taacctgccc cgttagttga agaaggtttt tatattacag ctccagatcc   3360
atatccttct ttttctgaac cgacttctcc ttttcgctt ctttattcca attgctttat    3420
tgacgttgag cctcggaacc cttaacaatc ccaaaacttg tcgaatggtc ggcttaatag   3480
ctcacgctat gccgacattc gtctgcaagt ttagttaagg gttcttctca acgcacaata   3540
```

```
aattttctcg gcataaatgc gtggtctaat ttttatttt aataaccttg atagcaaaaa    3600
atgccattcc aatacaaaac cacataccta taatcgacct gcaggaatta attcctccat    3660
tttcttctgc tatcaaaata acagactcgt gattttccaa acgagctttc aaaaaagcct    3720
ctgccccttg caaatcggat gcctgtctat aaaattcccg atattggctt aaacagcggc    3780
gcaatggcgg ccgcatctga tgtctttgct tggcgaatgt tcatcttatt tcttcctccc    3840
tctcaataat ttttcattc tatccctttt ctgtaaagtt tatttttcag aatactttta    3900
tcatcatgct ttgaaaaaat atcacgataa tatccattgt tctcacggaa gcacacgcag    3960
gtcatttgaa cgattttttt cgacaggaat tgccgggac tcaggagcat ttaacctaaa     4020
aaagcatgac atttcagcat aatgaacatt tactcatgtc tattttcgtt cttttctgta    4080
tgaaaatagt tatttcgagt ctctacggaa atagcgagag atgatatacc taaatagaga    4140
taaaatcatc tcaaaaaaat gggtctacta aatattatt ccatttatta caataaattc     4200
acagaatagt cttttaagta agtctactct gaatttttt a                         4241
```

<210> SEQ ID NO 8
<211> LENGTH: 382
<212> TYPE: PRT
<213> ORGANISM: Artificial
<220> FEATURE:
<223> OTHER INFORMATION: synthetic variant

<400> SEQUENCE: 8

```
Val Arg Ser Lys Lys Leu Trp Ile Ser Leu Leu Phe Ala Leu Ala Leu
1               5                   10                  15

Ile Phe Thr Met Ala Phe Gly Ser Thr Ser Ser Ala Gln Ala Ala Gly
            20                  25                  30

Lys Ser Asn Gly Glu Lys Lys Tyr Ile Val Gly Phe Lys Gln Thr Met
        35                  40                  45

Ser Thr Met Ser Ala Ala Lys Lys Lys Asp Val Ile Ser Glu Lys Gly
    50                  55                  60

Gly Lys Val Gln Lys Gln Phe Lys Tyr Val Asp Ala Ala Ser Ala Thr
65                  70                  75                  80

Leu Asn Glu Lys Ala Val Lys Glu Leu Lys Lys Asp Pro Ser Val Ala
                85                  90                  95

Tyr Val Glu Glu Asp His Val Ala His Ala Tyr Ala Gln Ser Val Pro
            100                 105                 110

Tyr Gly Val Ser Gln Ile Lys Ala Pro Ala Leu His Ser Gln Gly Tyr
        115                 120                 125

Thr Gly Ser Asn Val Lys Val Ala Val Ile Asp Ser Gly Ile Asp Ser
    130                 135                 140

Ser His Pro Asp Leu Lys Val Ala Gly Gly Ala Ser Met Val Pro Ser
145                 150                 155                 160

Glu Thr Asn Pro Phe Gln Asp Asn Asn Ser His Gly Thr His Val Ala
                165                 170                 175

Gly Thr Val Ala Ala Leu Asn Asn Ser Ile Gly Val Leu Gly Val Ala
            180                 185                 190

Pro Ser Ala Ser Leu Tyr Ala Val Lys Val Leu Gly Ala Asp Gly Ser
        195                 200                 205

Gly Gln Tyr Ser Trp Ile Ile Asn Gly Ile Glu Trp Ala Ile Ala Asn
    210                 215                 220

Asn Met Asp Val Ile Asn Met Ser Leu Gly Gly Pro Ser Gly Ser Ala
225                 230                 235                 240
```

Ala Leu Lys Ala Ala Val Asp Lys Ala Val Ala Ser Gly Val Val Val
            245                 250                 255

Val Ala Ala Ala Gly Asn Glu Gly Thr Ser Gly Ser Ser Ser Thr Val
        260                 265                 270

Gly Tyr Pro Gly Lys Tyr Pro Ser Val Ile Ala Val Gly Ala Val Asp
    275                 280                 285

Ser Ser Asn Gln Arg Ala Ser Phe Ser Ser Val Gly Pro Glu Leu Asp
290                 295                 300

Val Met Ala Pro Gly Val Ser Ile Gln Ser Thr Leu Pro Gly Asn Lys
305                 310                 315                 320

Tyr Gly Ala Leu Asn Gly Thr Ser Met Ala Ser Pro His Val Ala Gly
            325                 330                 335

Ala Ala Ala Leu Ile Leu Ser Lys His Pro Asn Trp Thr Asn Thr Gln
        340                 345                 350

Val Arg Ser Ser Leu Glu Asn Thr Thr Thr Lys Leu Gly Asp Ser Phe
    355                 360                 365

Tyr Tyr Gly Lys Gly Leu Ile Asn Val Gln Ala Ala Gln
370                 375                 380

<210> SEQ ID NO 9
<211> LENGTH: 1147
<212> TYPE: DNA
<213> ORGANISM: Bacillus subtilis

<400> SEQUENCE: 9
gtgagaagca aaaaattgtg gatcagtttg ctgtttgctt tagcgttaat ctttacgatg     60
gcgttcggca gcacatcctc tgcccaggcg gcagggaaat caaacgggga aagaaatat    120 attgtcgggt ttaaacagac aatgagcacg atgagcgccg ctaagagaaa gatgtcattt    180
ctgaaaaagg cgggaaagtg caaaagcaat tcaaatatgt agacgcagct tcagctacat    240
taaacgaaaa agctgtaaaa gaattgaaaa aagacccgag cgtcgcttac gttgaagaag    300
atcacgtagc acatgcgtac gcgcagtccg tgccttacgg cgtatcacaa attaaagccc    360
ctgctctgca ctctcaaggc tacactggat caaatgttaa agtagcggtt atcgacagcg    420
gtatcgattc ttctctcctg atttaaaggt agcaggcgga gccagcatgg ttccttctga    480
aacaaatcct ttccaagaca caactctca cggaactcac gttgccggca cagttgcggc    540
tcttaataac tcaatcggtg tattaggcgt tgcgccaagc gcatcacttt acgctgtaaa    600
agttctcggt gctgacggtt ccggccaata cagctggatc attaacggaa tcgagtgggc    660
gatcgcaaac aatatggacg ttattaacat gagcctcggc ggaccttctg gttctgctgc    720
tttaaaagcg gcagttgata aagccgttgc atccggcgtc gtagtcgttg cggcagccgg    780
taacgaaggc acttccggca gctcaagcac agtgggctac cctggtaaat acccttctgt    840
cattgcagta ggcgctgttg acagcagcaa ccaaagagca tctttctcaa gcgtaggacc    900
tgagcttgat gtcatggcac ctggcgtatc tatccaaagc acgcttcctg gaaacaaata    960
cggcgcgttg aacggtacat caatggcatc tccgcacgtt gccggagcgg ctgctttgat   1020
tctttctaag cacccgaact ggacaaacac tcaagtccgc agcagtttag aaaacaccac   1080
tacaaaactt ggtgattctt tctactatgg aaaagggctg atcaacgtac aggcggcagc   1140
tcagtaa                                                              1147

<210> SEQ ID NO 10
<211> LENGTH: 1170
<212> TYPE: DNA

<213> ORGANISM: Bacillus subtilis

<400> SEQUENCE: 10

```
atgagcacaa aaccttttta cagagatacg tgggcggaaa ttgacttgtc cgcgataaag        60
gaaaatgtca gcaatatgaa aaaacatatc ggtgaacatg tccacttgat ggcagttgtg       120
aaagcaaacg cctacgggca tggtgatgca gaaacagcaa aggctgctct tgacgcaggt       180
gcttcatgct tggccgtggc cattttggat gaagcgattt cactgcgcaa aaagggattg       240
aaggcgccta tattggtgct tggcgcggtt cccccggagt atgtggcaat cgctgctgag       300
tatgacgtga ccttaacagg ttattctgtt aatggcttc aggaggcagc ccgccacacg        360
aaaaaaggtt ctcttcattt tcatctgaag gtcgatacgg ggatgaacag acttggtgta       420
aaaacagagg aagaagttca aacgtgatg gcaattcttg accgcaaccc tcgtttaaag        480
tgcaaagggg tatttaccca ttttgcgaca gcggatgaaa agaaagagg ctatttctta        540
atgcagtttg agcgctttaa agagctgatt gctccgctgc cgttaaagaa tctaatggtc       600
cactgcgcga acagcgccgc tggactccgg ctgaaaaaag ctttttttaa tgcagtcaga       660
ttcggcatcg gcatgtatgg ccttcgcccg tctgctgaca tgtcggacga gataccgttt       720
cagctgcgtc cggcatttac cctgcattcg acactgtcac atgtcaaact gatcagaaaa       780
ggcgagagcg tcagctacgg agccgagtac acagcgaaa agacacatg atcgggacg          840
gtgcctgtag ctatgcgga cggctggctc gaaaattga agggaccga catccttgtg          900
aagggaaaac gcctgaaaat tgccggccga atttgcatgg accaatttat ggtggagctg       960
gatcaggaat atccgccggg cacaaaagtc acattaatag gccggcaggg ggatgaatat      1020
atttccatgg atgagattgc aggaaggctc gaaaccatta actatgaggt ggcctgtaca      1080
ataagttccc gtgttccccg tatgttttg gaaaatggga gtataatgga agtaagaaat       1140
cctttattgc aggtaaatat aagcaattaa                                       1170
```

<210> SEQ ID NO 11
<211> LENGTH: 389
<212> TYPE: PRT
<213> ORGANISM: Bacillus subtilis

<400> SEQUENCE: 11

```
Met Ser Thr Lys Pro Phe Tyr Arg Asp Thr Trp Ala Glu Ile Asp Leu
1               5                   10                  15

Ser Ala Ile Lys Glu Asn Val Ser Asn Met Lys Lys His Ile Gly Glu
            20                  25                  30

His Val His Leu Met Ala Val Val Lys Ala Asn Ala Tyr Gly His Gly
        35                  40                  45

Asp Ala Glu Thr Ala Lys Ala Ala Leu Asp Ala Gly Ala Ser Cys Leu
    50                  55                  60

Ala Val Ala Ile Leu Asp Glu Ala Ile Ser Leu Arg Lys Lys Gly Leu
65                  70                  75                  80

Lys Ala Pro Ile Leu Val Leu Gly Ala Val Pro Pro Glu Tyr Val Ala
                85                  90                  95

Ile Ala Ala Glu Tyr Asp Val Thr Leu Thr Gly Tyr Ser Val Glu Trp
            100                 105                 110

Leu Gln Glu Ala Ala Arg His Thr Lys Lys Gly Ser Leu His Phe His
        115                 120                 125

Leu Lys Val Asp Thr Gly Met Asn Arg Leu Gly Val Lys Thr Glu Glu
    130                 135                 140
```

Glu Val Gln Asn Val Met Ala Ile Leu Asp Arg Asn Pro Arg Leu Lys
145                 150                 155                 160

Cys Lys Gly Val Phe Thr His Phe Ala Thr Ala Asp Glu Lys Glu Arg
            165                 170                 175

Gly Tyr Phe Leu Met Gln Phe Glu Arg Phe Lys Glu Leu Ile Ala Pro
        180                 185                 190

Leu Pro Leu Lys Asn Leu Met Val His Cys Ala Asn Ser Ala Ala Gly
    195                 200                 205

Leu Arg Leu Lys Lys Gly Phe Phe Asn Ala Val Arg Phe Gly Ile Gly
210                 215                 220

Met Tyr Gly Leu Arg Pro Ser Ala Asp Met Ser Asp Glu Ile Pro Phe
225                 230                 235                 240

Gln Leu Arg Pro Ala Phe Thr Leu His Ser Thr Leu Ser His Val Lys
            245                 250                 255

Leu Ile Arg Lys Gly Glu Ser Val Ser Tyr Gly Ala Glu Tyr Thr Ala
        260                 265                 270

Glu Lys Asp Thr Trp Ile Gly Thr Val Pro Val Gly Tyr Ala Asp Gly
    275                 280                 285

Trp Leu Arg Lys Leu Lys Gly Thr Asp Ile Leu Val Lys Gly Lys Arg
290                 295                 300

Leu Lys Ile Ala Gly Arg Ile Cys Met Asp Gln Phe Met Val Glu Leu
305                 310                 315                 320

Asp Gln Glu Tyr Pro Pro Gly Thr Lys Val Thr Leu Ile Gly Arg Gln
            325                 330                 335

Gly Asp Glu Tyr Ile Ser Met Asp Glu Ile Ala Gly Arg Leu Glu Thr
        340                 345                 350

Ile Asn Tyr Glu Val Ala Cys Thr Ile Ser Ser Arg Val Pro Arg Met
    355                 360                 365

Phe Leu Glu Asn Gly Ser Ile Met Glu Val Arg Asn Pro Leu Leu Gln
370                 375                 380

Val Asn Ile Ser Asn
385

<210> SEQ ID NO 12
<211> LENGTH: 275
<212> TYPE: PRT
<213> ORGANISM: Bacillus subtilis

<400> SEQUENCE: 12

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

```
Pro Ser Gly Ser Ala Ala Leu Lys Ala Ala Val Asp Lys Ala Val Ala
    130                 135                 140

Ser Gly Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Leu Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275

<210> SEQ ID NO 13
<211> LENGTH: 4
<212> TYPE: PRT
<213> ORGANISM: Artificial
<220> FEATURE:
<223> OTHER INFORMATION: synthetic reagent

<400> SEQUENCE: 13

Ala Ala Pro Phe
1
```